US00PP28953P3

(12) United States Plant Patent
Kallsen et al.

(10) Patent No.: US PP28,953 P3
(45) Date of Patent: Feb. 13, 2018

(54) FEMALE PISTACHIO TREE NAMED 'GUMDROP'

(50) Latin Name: ***Pistacia vera* L.**
Varietal Denomination: Gumdrop

(71) Applicant: The Regents of the University of California, Oakland, CA (US)

(72) Inventors: Craig E. Kallsen, Davis, CA (US); Dan E. Parfitt, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/999,158

(22) Filed: Apr. 4, 2016

(65) Prior Publication Data

US 2016/0309632 P1 Oct. 20, 2016

Related U.S. Application Data

(60) Provisional application No. 62/147,539, filed on Apr. 14, 2015.

(51) Int. Cl.
*A01H 5/08* (2006.01)

(52) U.S. Cl.
USPC ..... Plt./152

(58) Field of Classification Search
USPC ..... Plt./152
See application file for complete search history.

(56) References Cited

PUBLICATIONS

Hickey (1973). "Classification of the Architecture of Dicotyledonous Leaves," American Journal of Botany, 60(1): 17-33.
Kallsen et al. (2017). "'Gumdrop', a New Early Harvest Pistachio Cultivar," Hortscience 52(2):310-312.
The Jun. 1, 2007 Test Agreement for Trees/Rootstocks (No. 2007-5037) between Aldo Antongiovanni and Sons and The Regents of The University of California, 8 pages.
The Aug. 1, 2011 Test Agreement for Trees (No. 2011-5024) between Gary Stiefvater and The Regents of The University of California, 7 pages.
The Jun. 1, 2014 Test Agreement for Trees and Rootstocks (No. 2014-5014) between Paramount Farming Company, LLC and The Regents of The University of California, 7 pages.
The Aug. 1, 2014 Test Agreement for Trees (No. 2014-5015) between Mid Valley Ranch, LLC and The Regents of The University of California, 8 pages.

*Primary Examiner* — Susan McCormick Ewoldt
(74) *Attorney, Agent, or Firm* — Morrison & Foerster LLP

(57) ABSTRACT

A new female pistachio tree (*Pistacia vera* L.) designated as 'Gumdrop', particularly characterized by early flowering time and early harvest date, is provided. The female pistachio tree 'Gumdrop' is further characterized by a high yield of nuts which meet commercial standards, maintaining a low percentage of loose shells and kernels.

40 Drawing Sheets

CROSS-REFERENCE TO RELATED APPLICATION

This application claims the benefit of U.S. Provisional Application No. 62/147,539, filed Apr. 14, 2015, which is incorporated herein by reference in its entirety.

Latin name: Botanical/commercial classification: *Pistacia vera* L.

Varietal denomination: The varietal denomination of the claimed pistachio variety is 'Gumdrop'.

BACKGROUND OF THE INVENTION

An objective of pistachio breeding programs is to develop new varieties that can be harvested at unique times relative to other pistachio varieties. The female pistachio variety 'Kerman' (not patented) is the main later-season pistachio cultivar grown in California and in other parts of the world, but other female pistachio varieties are also grown, such as 'Golden Hills' (U.S. Plant Pat. No. 17,158). A major problem for pistachio growers that has developed with the rapid increase in pistachio plantings in California, for example, is the availability of harvest equipment/contractors and processing capacity, since most of the existing crop ('Kerman')

matures at about the same time. The pistachio industry has ~40% of its orchards in non-bearing status, yet plantings have not slowed. Difficulty finding both harvesting equipment and people to run them at harvest time is a problem for pistachio growers. The industry-wide harvest window is short because of the large amount of future-bearing 'Kerman' plantings, all of which mature at about the same time. Nut processing facilities will likely need to greatly increase their capacity to handle this large increase in nuts, yet will use this increased capacity for a very short time period.

Further, 'Kerman' appears to be vulnerable to lack of winter chill, as shown directly through erratic bloom and indirectly from lack of overlap with this variety's pollenizer, 'Peters' (not patented). Low chill years have presented great difficulties for pistachio growers in the lower San Joaquin valley of California during periods when chilling was well below the minimum needed for synchronous flower development in 'Kerman'. High levels of "blanking" and non-splits were observed.

'Golden Hills' has become a popular alternative to 'Kerman' because it can be harvested before 'Kerman'. However, it would be advantageous to have additional varieties that can be harvested even earlier than 'Golden Hills' to increase the availability of pistachio harvesting equipment and processing capacity, as well as to have different pistachio varieties available that can be harvested in a maturity series. Developing a harvest date series is an optimal way to use existing harvest equipment/contractor and processing plant resources. Without staggered harvest dates, the pistachio industry will have to develop significantly increased (e.g. 2×) harvesting capability (which is now provided by custom harvestors) and find investors willing to fund new processing plants (which are only used for a few weeks per year). Failure to develop these facilities or alternatively, a harvest date series, will expose the industry to significant risk from aflatoxin contamination in the crop due to extended pre-processing times.

Thus, there exists a need for improved pistachio varieties with earlier harvest dates than the present industry standards. The present female pistachio variety 'Gumdrop' described herein is a product of the breeding efforts to produce improved pistachio varieties.

SUMMARY OF THE INVENTION

The present invention relates to a new and distinct pistachio cultivar (*Pistacia vera* L.) which has been denominated as 'Gumdrop', and more particularly as a female pistachio variety which exhibits earlier flowering and earlier harvest dates compared to the 'Golden Hills' and industry standard 'Kerman' cultivars.

'Gumdrop' produces a similar yield and percentage of split, edible nuts as 'Golden Hills' while maintaining a similar low percentage of loose shells and kernels. Nut quality and processed nut appearance of 'Gumdrop' is similar to other cultivars. Further, 'Gumdrop' exhibits very good yield, commercial level nut characteristics, and early harvest. 'Gumdrop' blooms about five days before 'Golden Hills' and 10-11 days before 'Kerman'. 'Gumdrop' matures about 12 days before 'Golden Hills' and about 24 days before 'Kerman'. The harvest date for 'Gumdrop' is about 10-12 days earlier than 'Golden Hills'. 'Gumdrop', 'Golden Hills', and 'Kerman' form a maturity series that spans nearly a month in the fall harvest season.

The earlier harvest date of 'Gumdrop' will permit pistachio growers to extend their harvest period and reduce competition for scarce harvesting resources. The earlier maturing date of 'Gumdrop' also makes it less susceptible to low chill effects and insect damage. Indeed, experience with 'Golden Hills' has shown that earlier harvest limits exposure of the crop to the last Navel Orangeworm (*Amyelois transitella*) flight, thereby significantly limiting potential aflatoxin contamination and crop loss issues. 'Gumdrop' has the earliest harvestable crop of any commercial cultivar, and also one of the earliest flowering times, suggesting that it may need less chilling than other commercial cultivars. This may be a very important characteristic in the future with respect to the warming climate.

'Gumdrop' was originally isolated as an open-pollinated offspring of 'B15-69' (not patented), the open-pollination having taken place in a pistachio breeding program test plot near Famoso, Calif., USA during Year 0. The initial seedling was identified and selected from a seedling trial located in Bakersfield, Calif., USA, and was originally designated as 'S-43'. Following initial identification, selection 'S-43' was initially asexually propagated in Bakersfield, Calif., USA as a single tree in July of Year 7. The second asexual propagation of 'S-43' took place in August of Year 7. Buds of 'S-43' were removed and grafted (using T-buds) into 'UCB-1' (not patented) seedling rootstocks at a trial plot located near Buttonwillow, Calif., USA. This trial contained three randomized and replicated plots of 'S-43' trees, with each plot containing six 'S-43' trees. Evaluation data were collected during Year 12-Year 14. Additional asexual propagations have occurred via T-budding at a test plot near Wasco, Calif., USA during Year 14. Selection 'S-43' was chosen as a candidate for release under the variety name 'Gumdrop'. The variety 'Gumdrop' has been found to be stable and reproduce true to type through successive asexual propagations.

BRIEF DESCRIPTION OF THE DRAWINGS

FIG. 9B and FIG. 9C illustrate the venation pattern on the leaves of 'Gumdrop'.

DETAILED BOTANICAL DESCRIPTION

The following is a detailed botanical description of the new female pistachio cultivar designated as 'Gumdrop', including the key differentiating characteristics of this variety and comparisons of certain characteristics of 'Gumdrop' to other pistachio varieties. Unless otherwise indicated, evaluation data was taken from 7- to 10-year-old trees. Color descriptions are based on the color standards presented in R.H.S. Colour Chart of The Royal Horticultural Society of London (R.H.S.) (1st edition, 1966).

Figure 10:
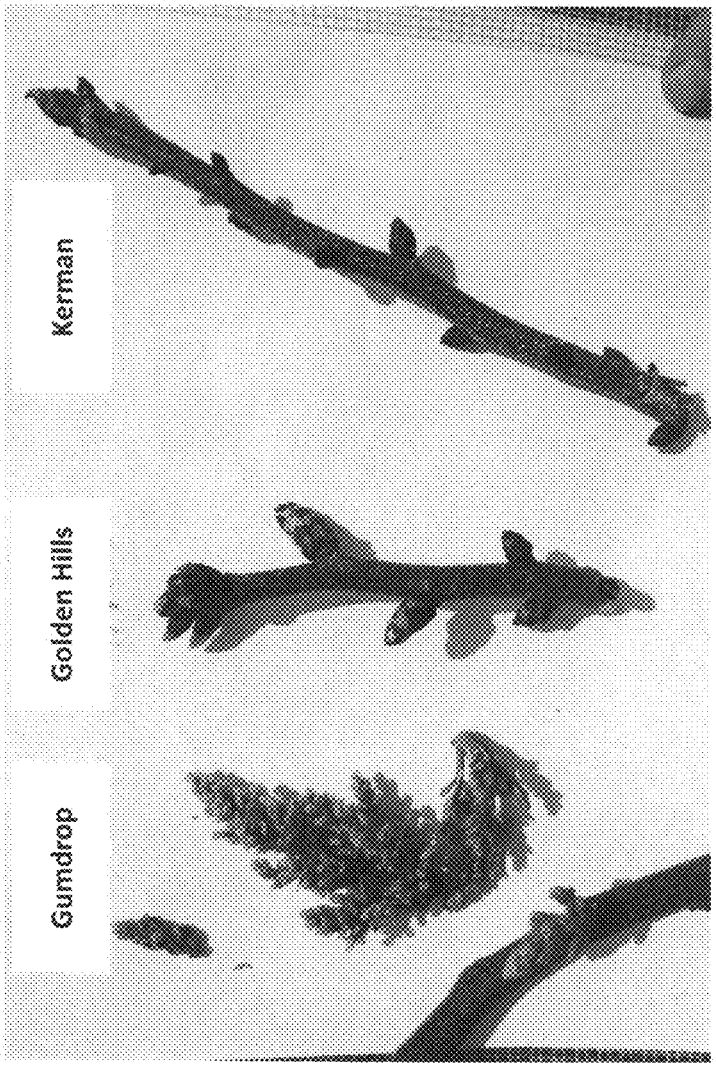
FIG. 10 illustrates the relative state of flower development on 8-year-old 'Gumdrop' trees vs. 'Golden Hills' and 'Kerman'.

Flowering Time: 'Gumdrop' is at full bloom five days before 'Golden Hills' and 10-11 days before 'Kerman'. The earlier development of flowers in 'Gumdrop' as compared to 'Golden Hills' and 'Kerman' is presented in FIG. 10.

Figure 1A:
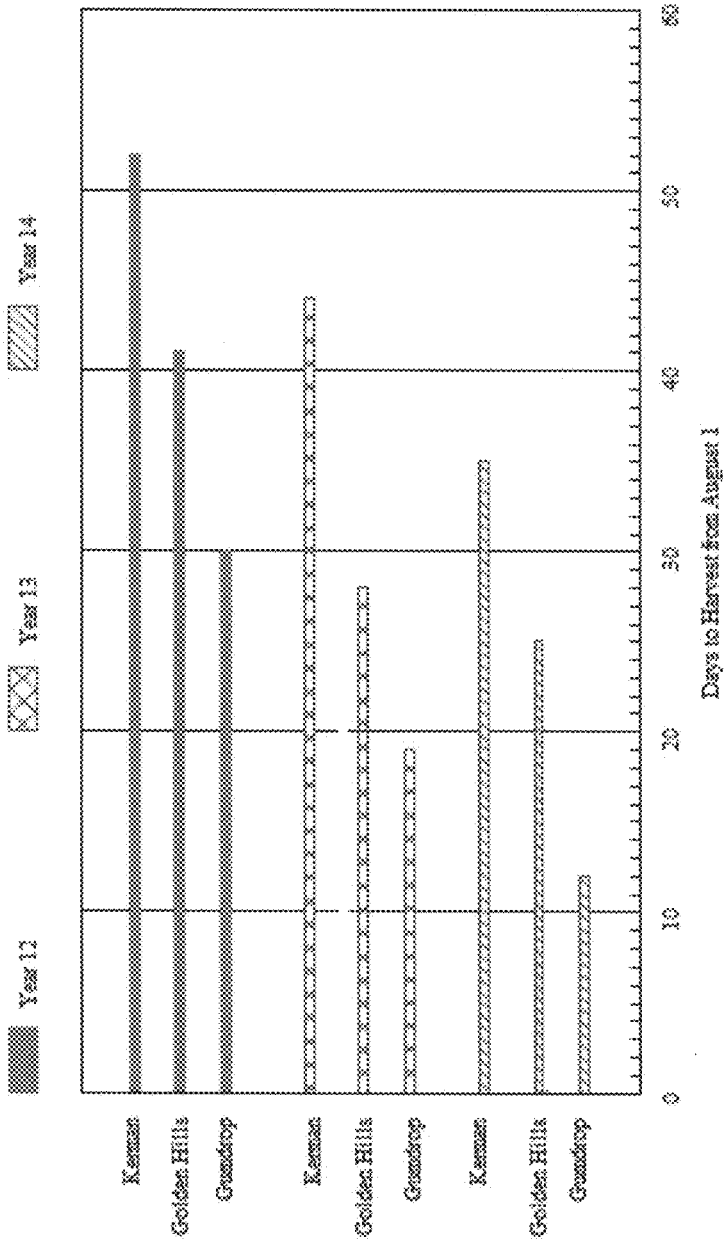
FIG. 1A illustrates mean days to harvest for 'Kerman', 'Golden Hills', and 'Gumdrop' over several years (Years 12-14).
Figure 1B:
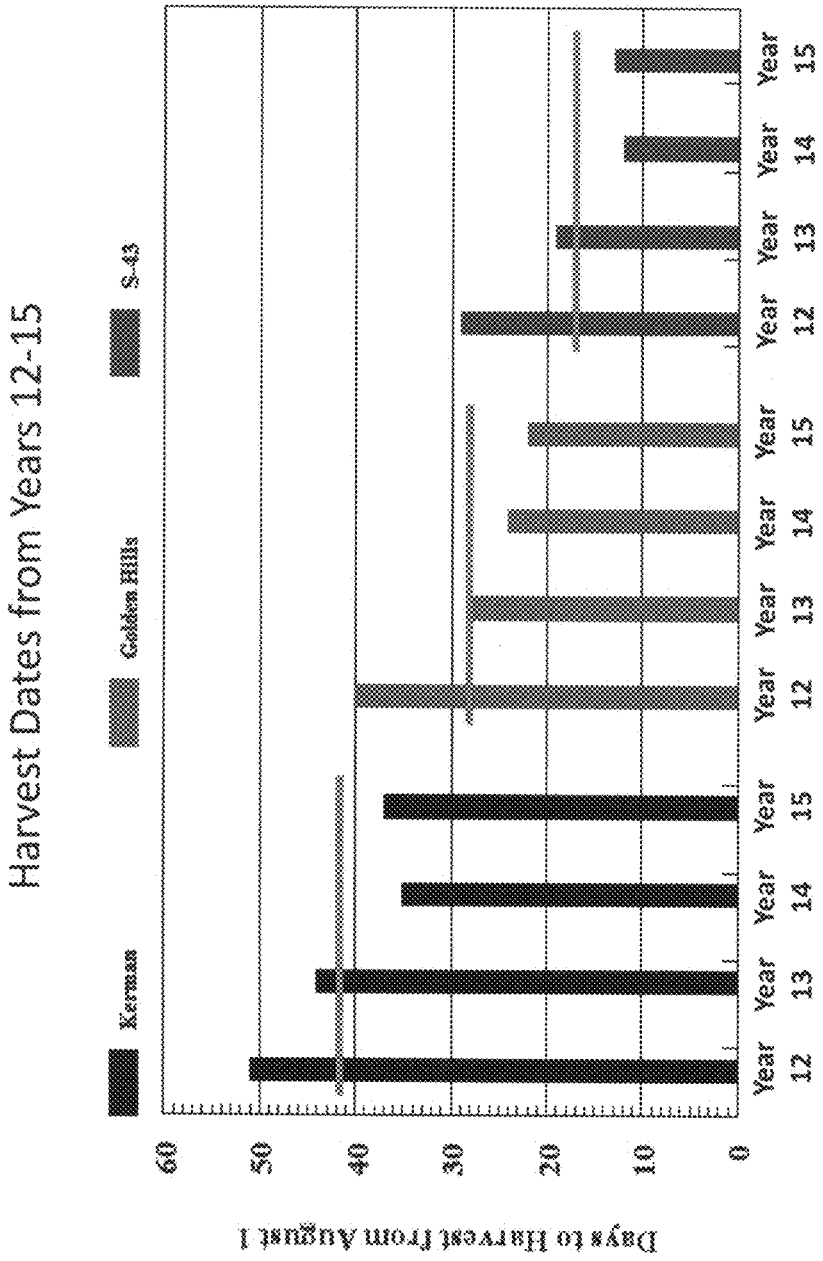
FIG. 1B illustrates mean days to harvest for 'Kerman', 'Golden Hills', and 'Gumdrop' ('S-43') over Years 12-15. Horizontal bar for each grouping of varieties denotes the grand harvest date mean for that variety over Years 12-15.
Figure 1C:
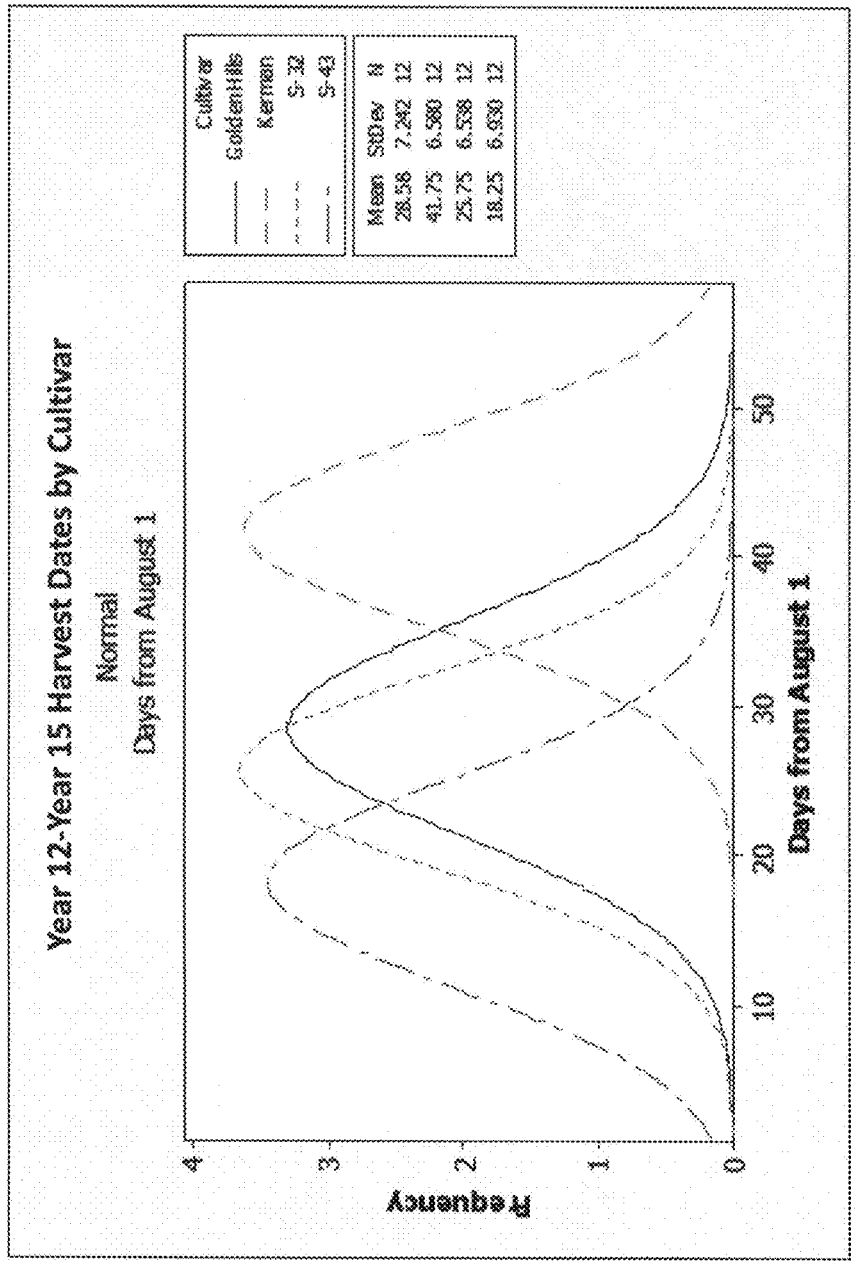
FIG. 1C illustrates combined harvest date data for all years (Years 12-15) by cultivar fitted to normal distributions. 'Gumdrop' trees were 5 years old in Year 12.

Harvest Date: 'Gumdrop' matures much earlier than 'Golden Hills' and 'Kerman'. The harvest date for 'Gumdrop' is about 10-12 days earlier than 'Golden Hills' and 24 days before 'Kerman' (FIG. 1A). This is a valuable commercial characteristic, as it allows increased availability of harvest equipment/contractors and processing capacity. FIG. 1B illustrates harvest date data for multiple female selections, including 'Gumdrop' ('S-43'), during Years 12-15. FIG. 1C demonstrates how 'Gumdrop' fits into a harvest series for the pistachio industry, and further illustrates the earlier average harvest time of this variety as compared to either 'Kerman' or 'Golden Hills'.

Plant winter hardiness, heat tolerance, and drought tolerance: 'Gumdrop' will tolerate temperatures greater than −5° C. to −10° C., as is typical of *Pistacia vera* L. The 'UCB-1' rootstock on which it is grafted, however, can sustain significant damage at −5° C. after a few hours. The 'Gumdrop' cultivar is typically grown in a hot dry environment, and has been grown in a location having typical summer temperatures greater than 40° C. to 42° C. 'Gumdrop' requires hot days with temperatures greater than 30° C. to ripen the fruit. 'Gumdrop' does not require as much heat (in terms of heat units) to reach maturity as 'Golden Hills' or 'Kerman'. Without wishing to be bound by theory, it is thought that this is why the harvest date of 'Gumdrop' is approximately 24 days earlier than 'Kerman'. All California pistachio cultivars are grown as an irrigated crop and require about 1000 mm of water during the growing season. Pistachio cultivars will tolerate poor quality water and do not show significant yield loss or damage up to EC (electrical conductivity) 8-12.

Figure 9A:
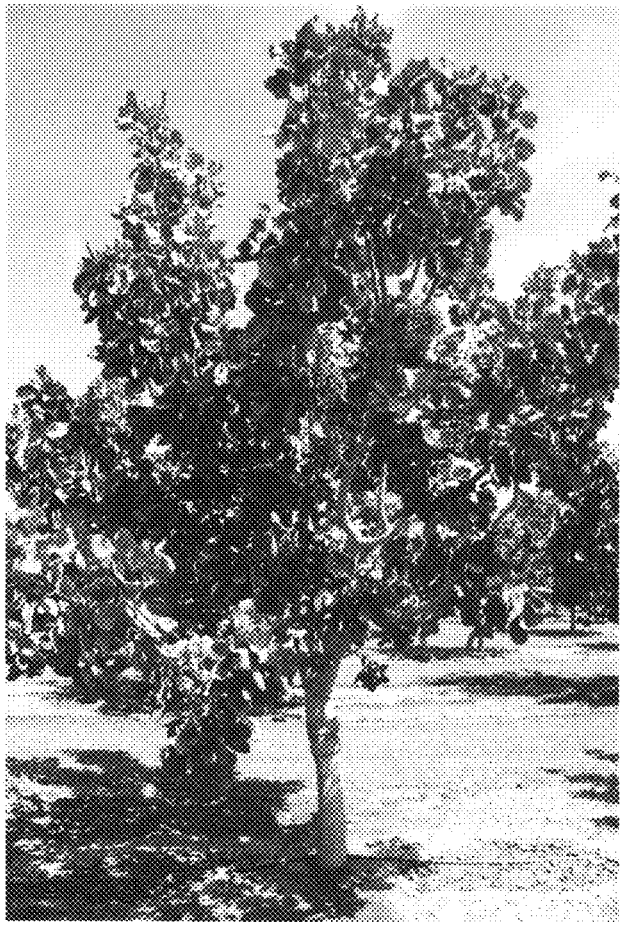
FIG. 9A illustrates the trunk, branches, and canopy of 8-year-old 'Gumdrop' trees.

Tree: 'Gumdrop' is a large vigorous tree relative to 'Golden Hills' or 'Kerman' when grown on 'UCB-1' rootstock. An image of a 'Gumdrop' tree, including images of the trunk, branches, and canopy, is presented in FIG. 9A. A detailed evaluation of tree size is provided below. Scaffold branches are observed to be larger and fewer in number than for 'Golden Hills' but are similar to 'Kerman' with scaffold branch angled 80 to 90 degrees with respect to the trunk. Primary and secondary branches are stiff, which facilitates shaking for harvest.

Tree size: 'Gumdrop' is a large and vigorous tree. Pistachio tree height and shape may be controlled by pruning. 'Gumdrop' tree height was approximately 2-3 meters in Year 17 (10-year-old trees). 'Kerman' and 'Golden Hills' were used for comparisons, and all cultivars were similar in size (not significantly different). Tree size was evaluated in terms of trunk cross sectional area. A meaningful evaluation of tree size is the trunk cross sectional area (Table 1A and Table 1B). Values were taken as circumferences measured 10 cm above and below the graft union, and the units of the circumferences are in centimeters. The formulas used to convert the circumference measurements to cross sectional areas are circumference$=\pi 2r=\pi d$ and area$=\pi r^2=\pi(d/2)^2$.

TABLE 1A

Analysis of Variance for Trunk Cross Sectional Area

| Source | DF | Adj MS | F | P |
|---|---|---|---|---|
| For scion (cultivar): | | | | |
| Cultivar | 2 | 134051 | 28.88 | 0.000 |
| Block | 2 | 721 | 0.16 | 0.857 |
| Error | 43 | 4642 | | |
| Total | 47 | | | |
| S = 68.1345 | | | | |
| R-Sq = 57.45% | | | | |
| R-Sq(adj) = 53.49% | | | | |
| For rootstock: | | | | |
| Cultivar | 2 | 16413 | 3.86 | 0.029 |
| Block | 2 | 513 | 0.12 | 0.887 |
| Error | 43 | 4257 | | |
| Total | 47 | | | |
| S = 65.2430 | | | | |
| R-Sq = 15.61% | | | | |
| R-Sq(adj) = 7.76% | | | | |

TABLE 1B

Mean differences for Trunk Cross Sectional Area ($cm^2$, lower diagonal) and P values (upper diagonal) for Bonferroni pairwise comparisons of scion and rootstock

| | Golden Hills | Kerman | S-43 |
|---|---|---|---|
| For scion (cultivar): | | | |
| Golden Hills | — | 1.0000 | 0.0000 |
| Kerman | −4.4 | — | 0.0000 |
| S-43 (Gumdrop) | 152.6 | −157.0 | — |
| For rootstock: | | | |
| Golden Hills | — | 1.0000 | 0.0275 |
| Kerman | 18.5 | — | 0.3013 |
| S-43 (Gumdrop) | 59.4 | −40.8 | — |

Bark: Bark color is gray, similar to 'Kerman' and 'Golden Hills' (202C to 202D). Bark lenticels were evaluated in Year 14 (7-year-old trees) by counting the number of lenticels on 'Gumdrop', 'Kerman', and 'Golden Hills'. 5-7 observations per 5 $cm^2$ were obtained from at least 4 trees per cultivar. Significant qualitative differences were observed among the cultivars. 'Gumdrop' has an abundance of relatively smooth compound lenticels arranged in horizontal rows of 3 to 4 together. 'Golden Hills' has much more prominent rough individual lenticels, arranged in a much more irregular manner. 'Kerman' lenticels are more regularly arranged but are fewer in number and with a much smoother appearance than for either 'Gumdrop' or 'Golden Hills'. 'Gumdrop' had a significantly higher density of lenticels than the other cultivars (Table 2A and Table 2B).

TABLE 2A

GLM ANOVA for number of lenticels per $cm^2$ of bark.

| Source | DF | MS | F | P |
|---|---|---|---|---|
| Cultivar | 2 | 46.756 | 5.27 | 0.000 |
| Error | 15 | 3.063 | | |
| Total | 17 | | | |

TABLE 2B

Mean differences for lenticel density (lower diagonal) and P values (upper diagonal) for Bonferroni pairwise comparisons.

| | Golden Hills | Kerman | S-43 |
|---|---|---|---|
| Golden Hills | — | 0.1680 | 0.011 |
| Kerman | −2.190 | — | 0.0000 |
| S-43 (Gumdrop) | 3.340 | 5.530 | — |

Figure 9B:
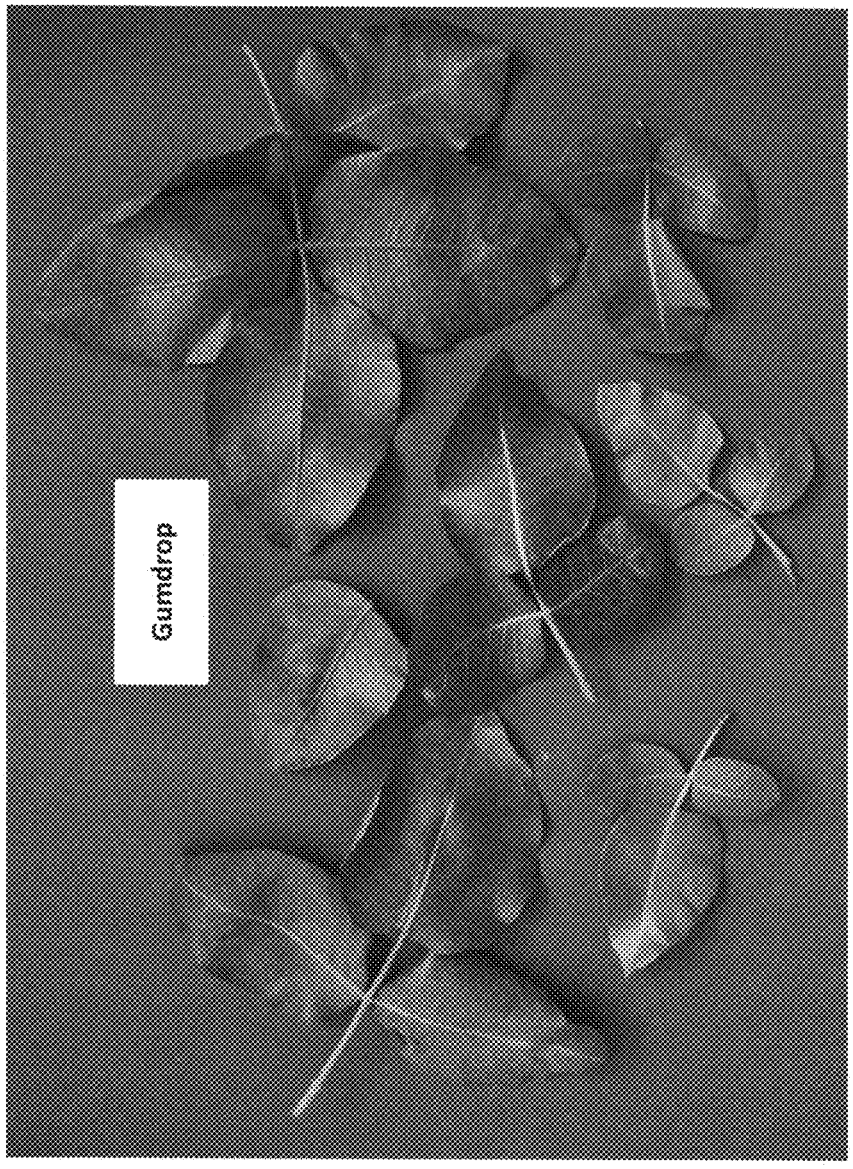
FIG. 9B illustrates the leaves of 8-year-old 'Gumdrop' trees.
Figure 9C:
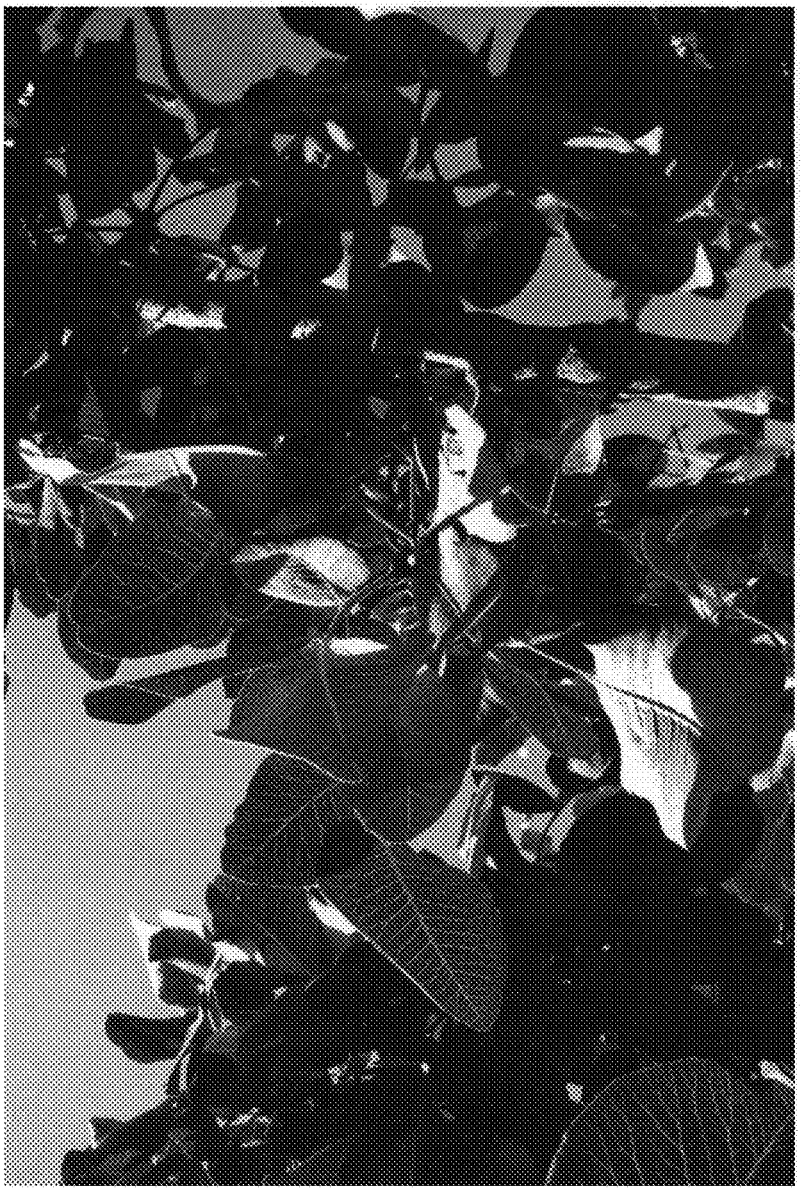
FIG. 9C, FIG. 9D, FIG. 9E, and FIG. 9F illustrate leaves at maturity on 10-year-old 'Gumdrop' trees.
Figure 9D:
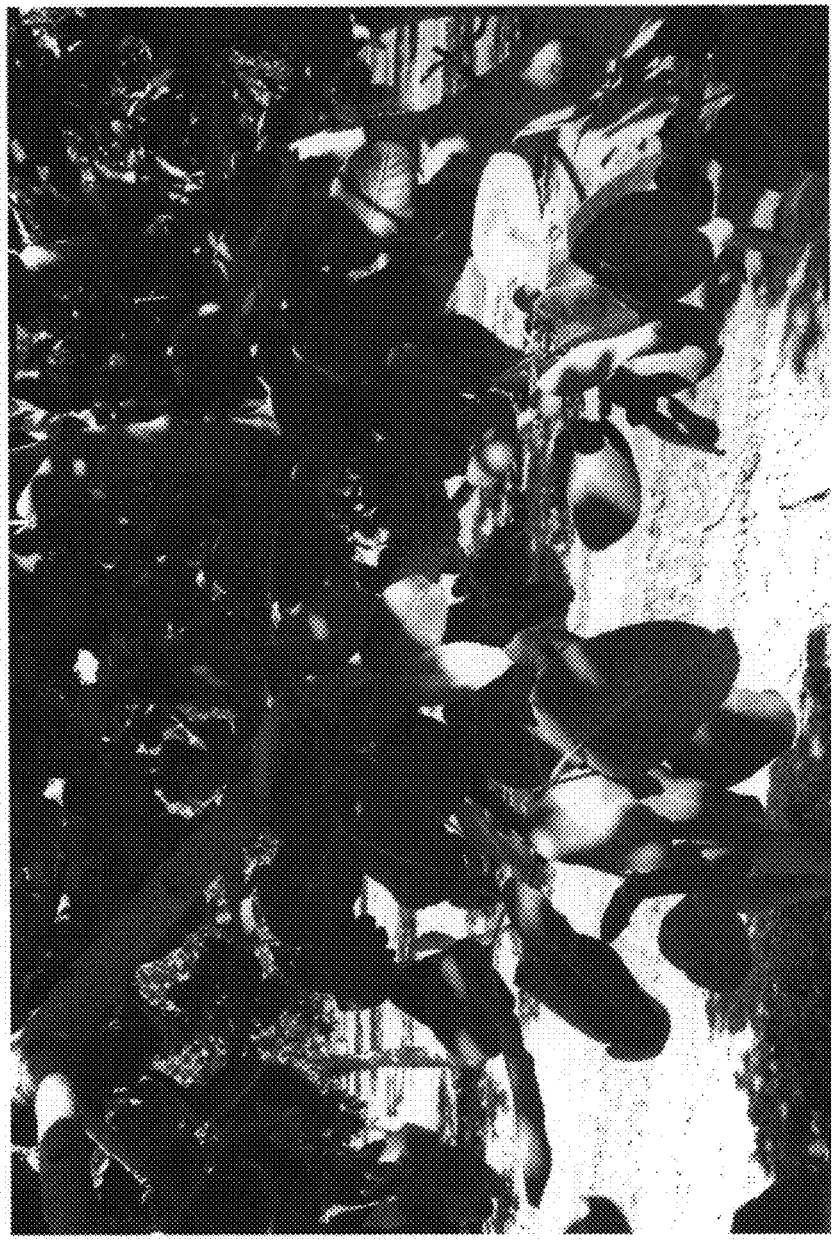
Figure 9E:
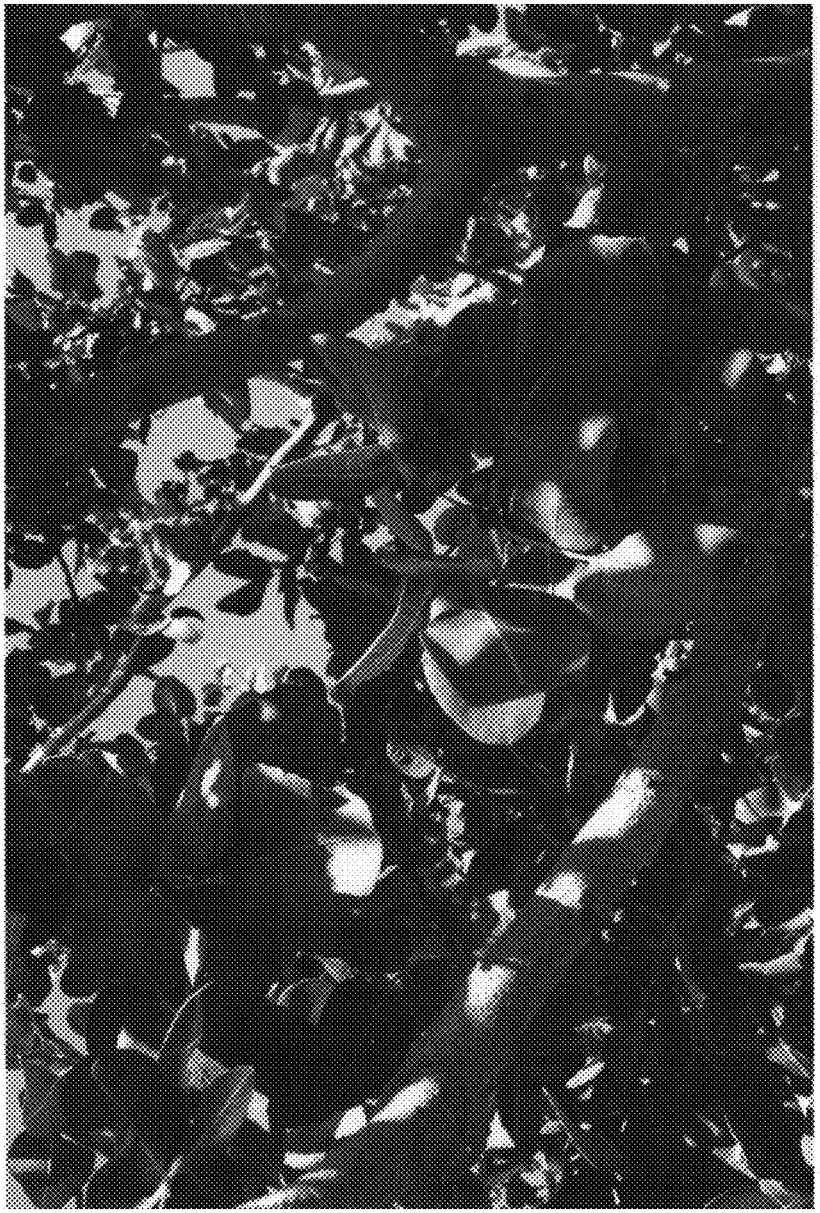
Figure 9F:
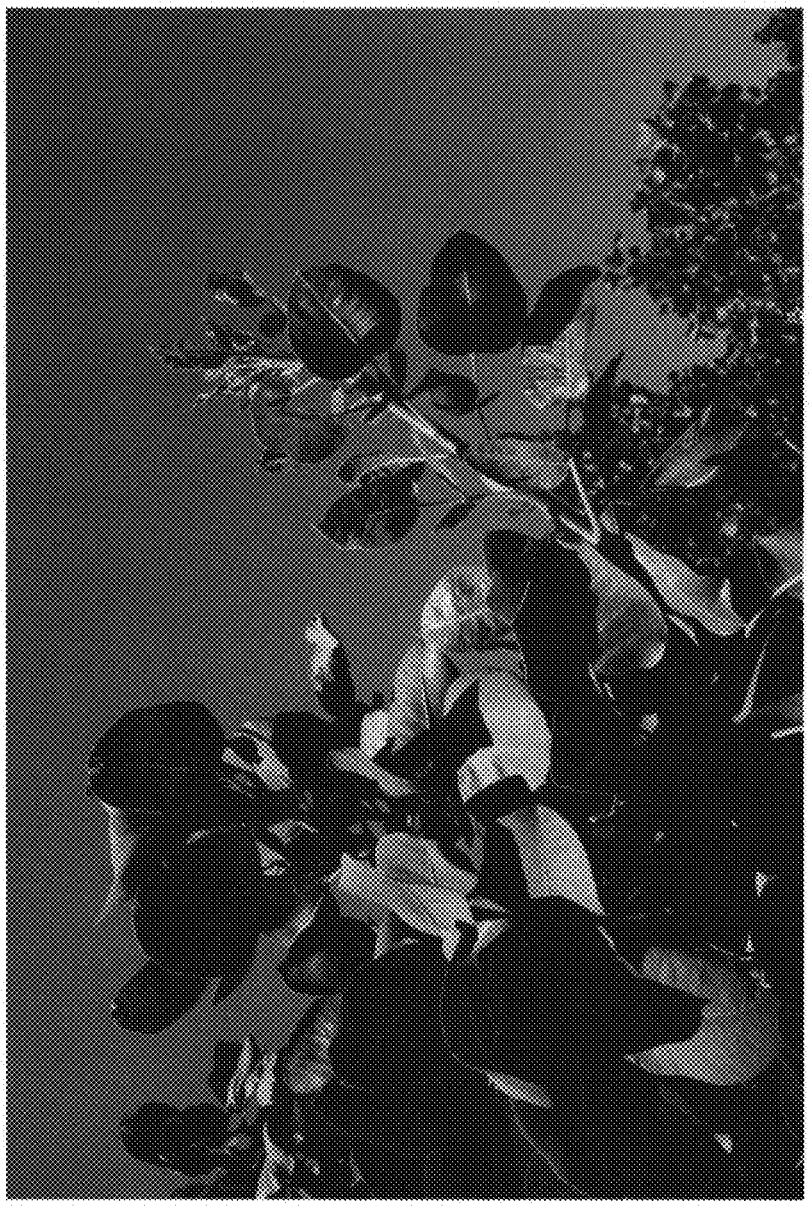

Leaves: Images of the leaves of 'Gumdrop' are presented in FIG. 9B, FIG. 9C, FIG. 9D, FIG. 9E, and FIG. 9F. Leaves are highly variable in the details of their form, shape and size within the tree. In general, the leaves are deciduous simple compound imparipinnate with one or two pairs of oppositely arranged lateral leaflets. However, the leaves can also be trifoliate and on branches with an abundance of new vegetative growth, and only one or no lateral leaflets may be present. Leaflet margins are entire to slightly crenate. Leaf and leaflet sizes are highly variable. Leaflets are oval to ovate and 5-8 cm long. Terminal leaflets can be less than 8 cm to greater than 16 cm. Leaflets vary considerably in shape, in general being ovate with cuspidate to rounded apex and rounded base (FIG. 9B). Leaflets are somewhat larger than for 'Kerman' and 'Golden Hills'. Margins of leaf blades are entire. Leaf surfaces are glabrous, smooth, and waxy. Leaf venation is of the cladodromous type as described by Hickey (1973) Amer. J. Botany 60:17-33 (FIG. 9B and FIG. 9C). For leaves, color evaluations were done on at least 3 leaves, each new and mature, collected at random from a 'Gumdrop' tree. Mature leaves are various shades of green, top surface=139B, bottom surface=139B, new leaves, top surface=138B, 139C, bottom surface=139C, leaf midrib/petiole=143C. Leaves range from light green at first emergence to dark green at maturity with no difference between upper and lower leaf surfaces. Petioles may be 30 mm to more than 60 mm in length to the first lateral. The petiole diameter is approximately 1-2 mm, and therefore too small to be measured accurately. Typical petiole/leaf values are shown in Table 3 (15 observations) for Year 17 data from the plot at Buttonwillow, Calif., USA. Differences were tested at 5% level for both petiole and terminal leaflets. Gumdrop had significantly shorter petioles than Golden Hills (p=0.032). Terminal leaflet length was also highly significant (p=0.002) with Gumdrop being significantly smaller than Kerman (Tukey test 5%).

TABLE 3

Typical petiole/leaf values from Year 17

| Cultivar | Variable | Mean | SD | p-value |
|---|---|---|---|---|
| Gumdrop | petiole length (cm) | 3.99 | 1.06 | 0.012 |
| G. Hills | petiole length (cm) | 5.06 | 0.89 | |
| Kerman | petiole length (cm) | 4.64 | 0.89 | |
| Gumdrop | terminal leaflet (cm) | 10.73 | 1.55 | 0.002 |
| G. Hills | terminal leaflet (cm) | 9.14 | 2.04 | |
| Kerman | terminal leaflet (cm) | 11.64 | 1.91 | |

Flowers, inflorescences, and fruits: 'Gumdrop' bears female flowers on inflorescences, which are panicles with 8-15 branches borne on the prior year's wood in the spring. Each inflorescence contains 50-200 flowers. However, only 20-80 flowers develop into fruit. Inflorescences vary greatly in size from less than 1 cm long at budbreak to greater than 5 cm long at full expansion. The width of inflorescences varies from 0.5 cm at budbreak to greater than 3 cm fully expanded. Flowers are receptive when the inflorescence is greater than 2 cm. Individual flowers are 1-2 mm long. Petals and nectaries are missing and sepals are much reduced, with most of the flower consisting of stigma and style and a single superior ovary. Fruits are drupes with a fleshy exocarp/mesocarp and a hard endocarp enclosing the seed. The endocarp typically splits longitudinally from the stylar end.

Figure 2A:
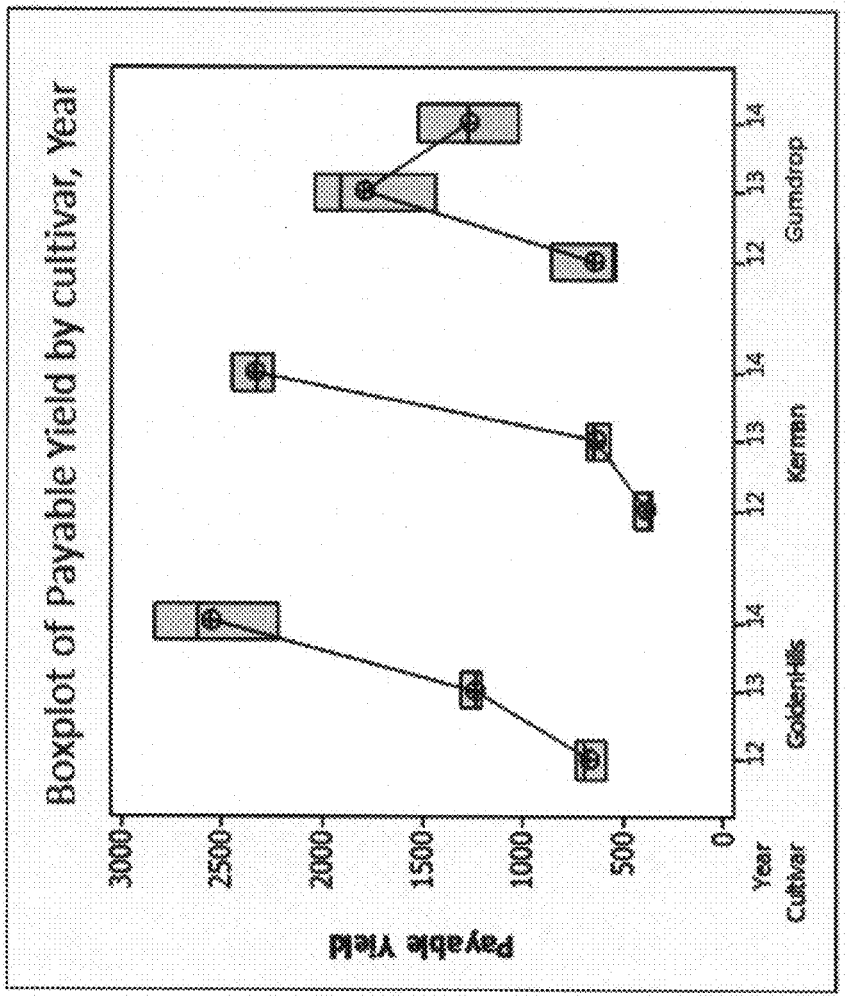
FIG. 2A illustrates payable yield (pounds per acre, lb/ac) for 'Golden Hills', 'Kerman', and 'Gumdrop' over several years (Years 12-14).

Yield: Total edible yield is the weight of in-shell edible split nuts (nuts and shell) in addition to the kernels that come from shelling stock and closed shells. This is also called grower paid yield or payable yield. 'Gumdrop' yielded significantly more nuts than 'Kerman' (2.4×) and 'Golden Hills' (1.3×) in the first two years of replicated trials. 'Gumdrop' had a mean payable yield of 1239 lb/ac over the first 3 years of harvested yield (Years 12-14), similar to 'Golden Hills' (1492 lb/ac) and better but not significantly different (Bonferroni, Tukey tests) yield than 'Kerman' (1121 lb/ac) (FIG. 2A). 'Gumdrop' yield was reduced in Year 14 due to high yield in Year 13, while 'Golden Hills' and 'Kerman' did not begin to bear significantly until the third harvest (Year 14) (FIG. 2A). These differences reflect better early yield for 'Gumdrop' and consequent earlier initiation of the alternate bearing cycle.

Figure 2B:
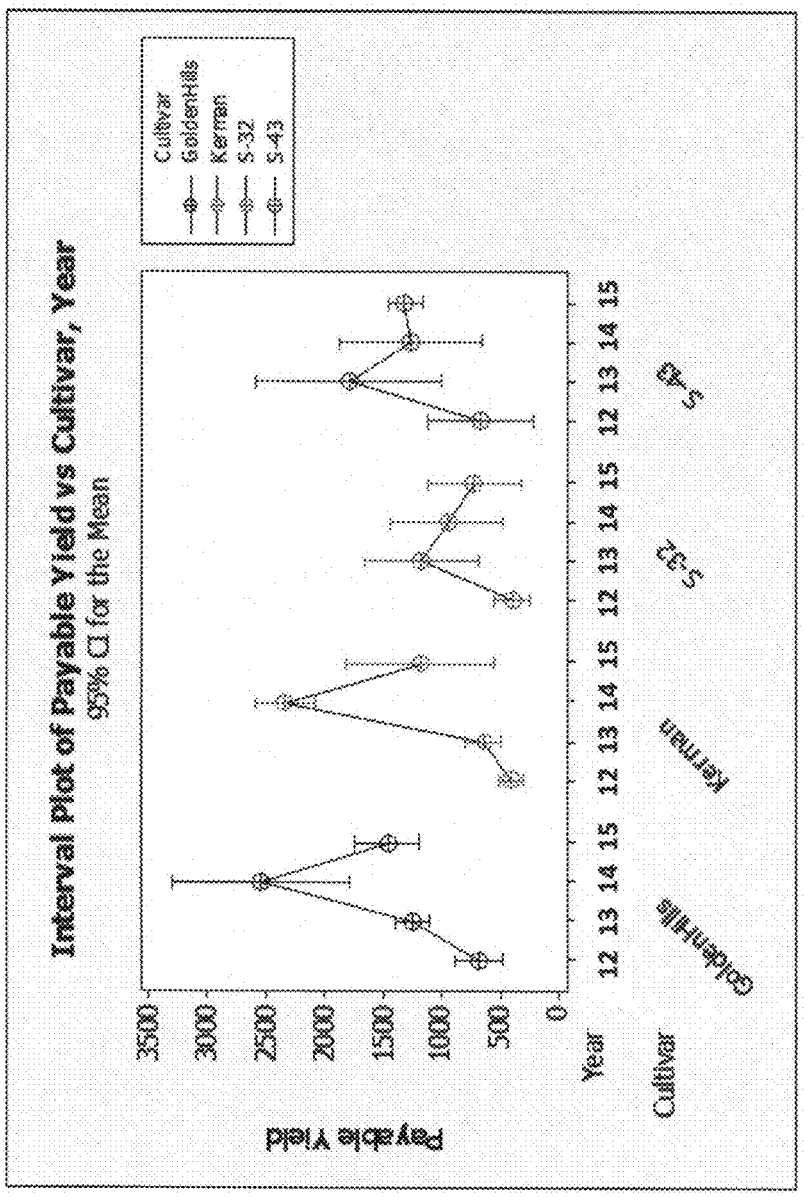
FIG. 2B illustrates payable yield (lb/ac) for 'Golden Hills', 'Kerman', 'Gumdrop' ('S-43'), and 'S-32' (not patented) over several years (Years 12-15).
Figure 2C:
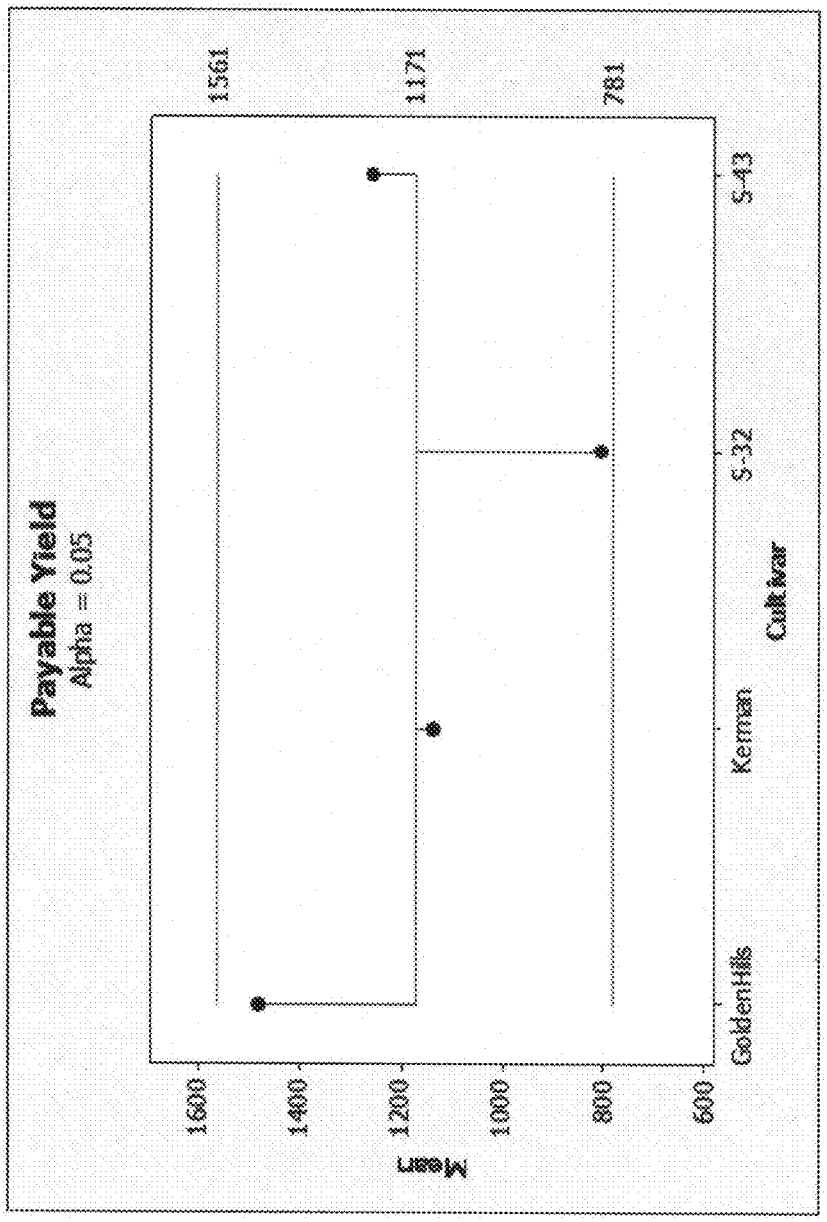
FIG. 2C illustrates mean payable yield (lb/ac) for 'Golden Hills', 'Kerman', 'Gumdrop' ('S-43'), and 'S-32' over several years (Years 12-15). 'Gumdrop' trees were 5 years old in Year 12.

Based on data from Years 12-15, 'Gumdrop' had a mean payable yield of 1256 lb/ac over the first 4 years of harvested yield (Years 12-15), less than 'Golden Hills' (1484 lb/ac), and better but not significantly different (Bonferroni, Tukey) than 'Kerman' (1134 lb/ac). An analysis and statistics summary is provided in Table 4A and Table 4B. The 95% confidence interval plot in FIG. 2B shows that 'Gumdrop' ('S-43') yield was reduced in Year 14 due to high yield in Year 13, but had better yield in Year 15 than 'Kerman', suggesting that it may be less susceptible to alternate bearing than 'Kerman' or 'Golden Hills', with performance characteristics more typical of 'Lost Hills'. All values are based on an industry harvest practice of shaking the trees to obtain the nuts. No attempt was made to remove any adhering nuts after shaking. Mean payable yields for the various varieties analyzed during Years 12-15 are shown in FIG. 2C.

TABLE 4A

Analysis of Variance for Payable Yield

| Source | DF | MS | F | P |
|---|---|---|---|---|
| Cultivar | 3 | 954866 | 28.50 | 0.000 |
| Year | 3 | 3149551 | 94.02 | 0.000 |
| Cultivar*Year | 9 | 654280 | 19.53 | 0.000 |
| Block | 2 | 4915 | 0.15 | 0.864 |
| Error | 30 | 33500 | | |
| Total | 47 | | | |

S = 183.030
R-Sq = 94.77%
R-Sq(adj) = 91.81%

TABLE 4B

Mean differences for payable yield (lb/ac, lower diagonal) and P values (upper diagonal) for Bonferroni pairwise comparisons.

| | Golden Hills | Kerman | S-32 | S-43 |
|---|---|---|---|---|
| Golden Hills | — | 0.0003 | 0 | 0.0289 |
| Kerman | −350 | — | 0.0008 | 0.6787 |
| S-32 | −677 | −327 | — | |
| S-43 (Gumdrop) | −228 | 122 | 449 | — |

Color of nuts: For 'Gumdrop' nuts, evaluations were done on 3 or more nuts, using The R.H.S. Colour Chart 1st edition for color standards, as described above. Husks as described are the exocarp outside of the shells, and kernel values are taken after shell removal. Husk color gradually changes from a light green in late June to a cream white (149D, 150D, some 145D) with a pinkish tip at the distal end near maturity (149D, 150D, some 145D) and stem end scores of 149D, 150D, and some 145D.

Figure 3A:
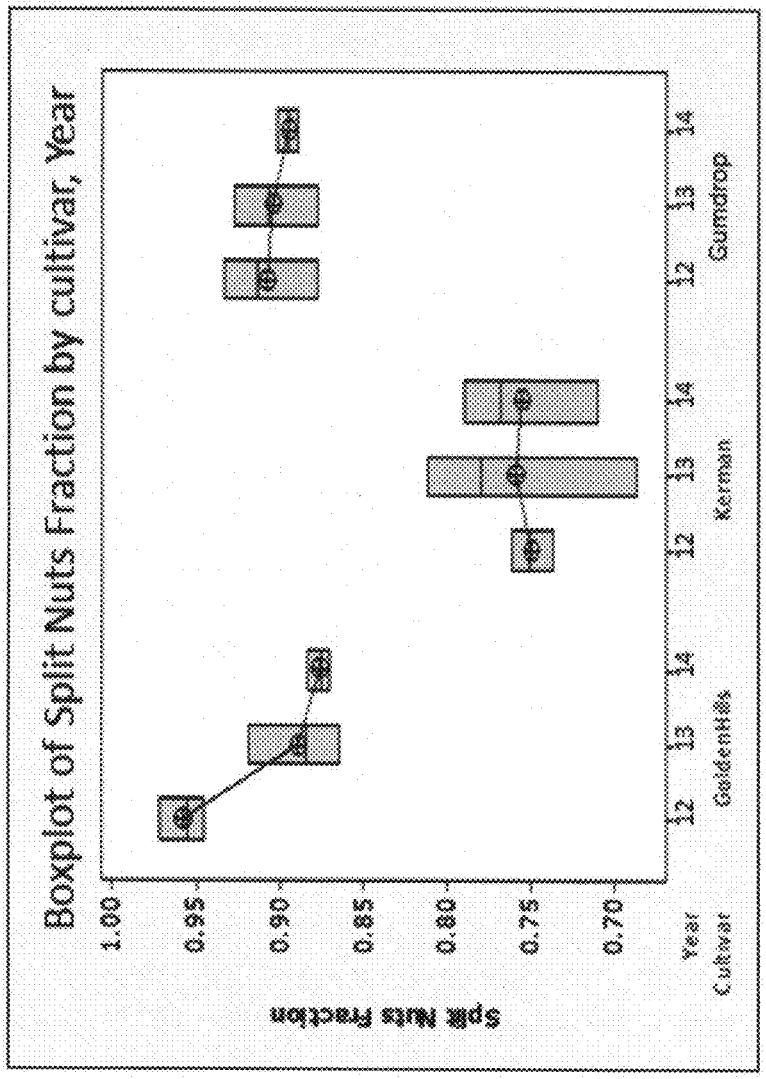
FIG. 3A illustrates fraction of split nuts for 'Golden Hills', 'Kerman', and 'Gumdrop' over several years (Years 12-14).

Nut Characteristics, Split nuts/Non-split nuts: Based on data from Years 12-14, 'Gumdrop' had a very high split percentage (90.2%), similar to 'Golden Hills' (90.7%) and significantly better (Bonferroni, Tukey tests) than 'Kerman' (75.6%) (FIG. 3A). Cultivars that split well are desired by growers since they receive substantially higher payment for naturally split nuts. Non-splits are usually processed for kernels to be used in confections.

Figure 3B:
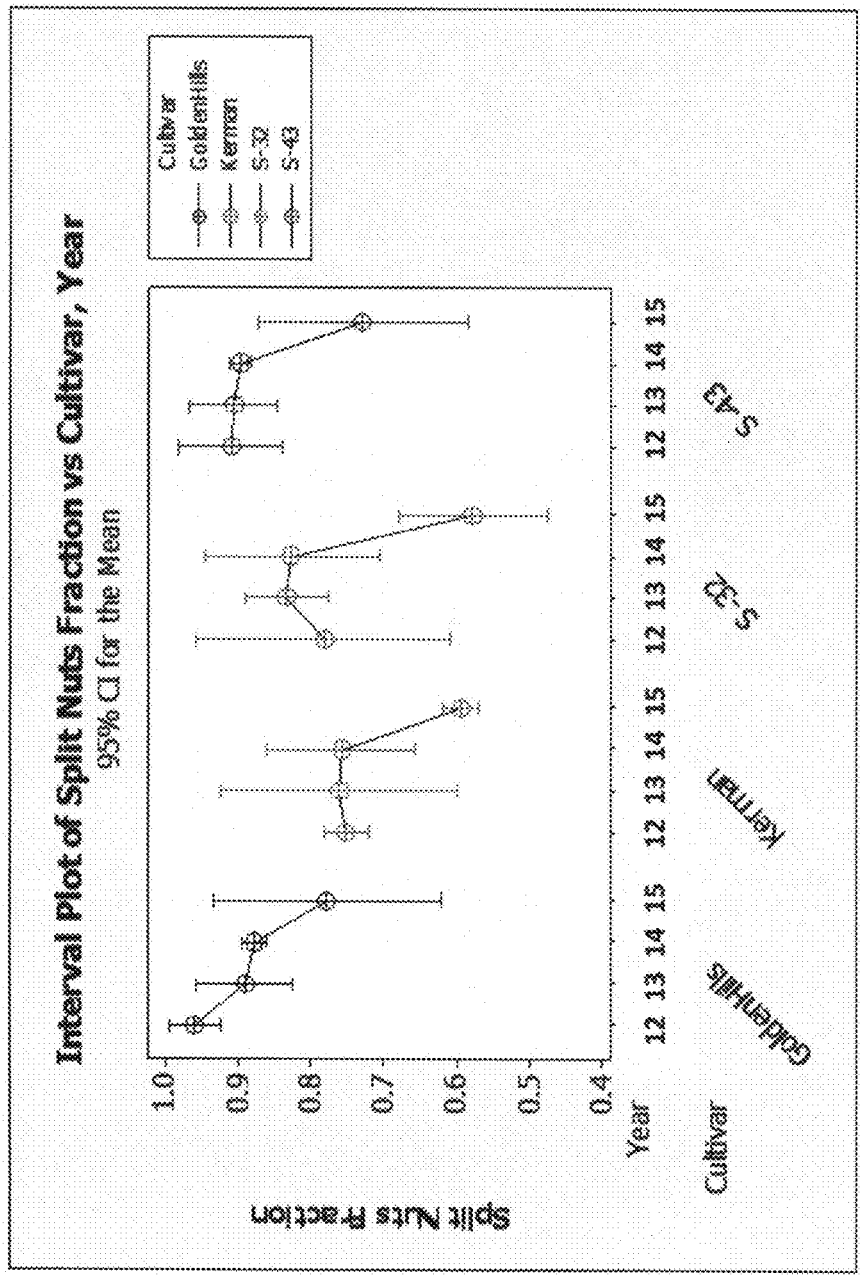
FIG. 3B illustrates fraction of split nuts for 'Golden Hills', 'Kerman', 'Gumdrop' ('S-43'), and 'S-32' over several years (Years 12-15).
Figure 3C:
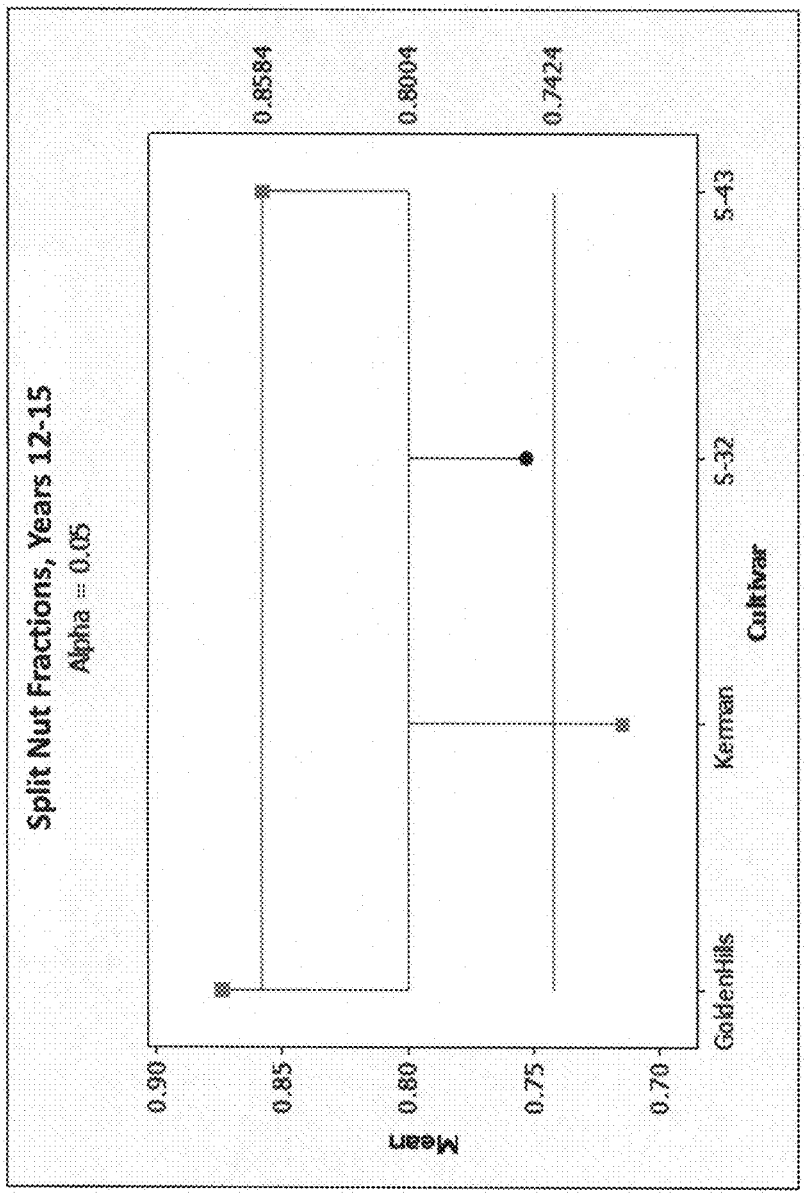
FIG. 3C illustrates an analysis of means for split nut fraction for 'Golden Hills', 'Kerman', 'Gumdrop' ('S-43'), and 'S-32' over several years (Years 12-15). 'Gumdrop' trees were 5 years old in Year 12.

Based on data from Years 12-15, 'Gumdrop' had a very high split percentage (85.8%), similar to 'Golden Hills' (87.4%) and significantly better (Bonferroni test) than 'Kerman' (71.4%). An analysis and statistics summary is provided in Table 5A and Table 5B. These differences were especially notable during Year 15 (FIG. 3B), when 'Kerman' showed a very high non-split percentage, as well as low yields. Split percentage for 'Gumdrop' was comparable to 'Golden Hills' (FIG. 3C), which is the "gold standard" for splits. Split percentages were generally low in Year 15 for all varieties analyzed due to insufficient chilling, producing more blanks, etc.

TABLE 5A

Analysis of Variance for Split Nut Fractions

| Source | DF | MS | F | P |
|---|---|---|---|---|
| Cultivar | 3 | 0.073604 | 44.24 | 0.000 |
| Year | 3 | 0.094055 | 56.54 | 0.000 |
| Cultivar*Year | 9 | 0.003199 | 1.92 | 0.087 |
| Block | 2 | 0.000353 | 0.21 | 0.810 |
| Error | 30 | 0.001664 | | |
| Total | 47 | | | |

S = 0.0407876
R-Sq = 91.43%
R-Sq(adj) = 86.57%

TABLE 5B

Mean differences for fraction of split nuts (lower diagonal) and P values (upper diagonal) for Bonferroni pairwise comparisons

| | Golden Hills | Kerman | 5-32 | S-43 |
|---|---|---|---|---|
| Golden Hills | — | 0.0000 | 0.0000 | 1.0000 |
| Kerman | −0.16 | — | 0.1575 | 1.0000 |
| S-32 | −0.121 | 0.039 | — | 0.0000 |
| S-43 (Gumdrop) | −0.012 | 0.144 | 0.105 | — |

Figure 4A:
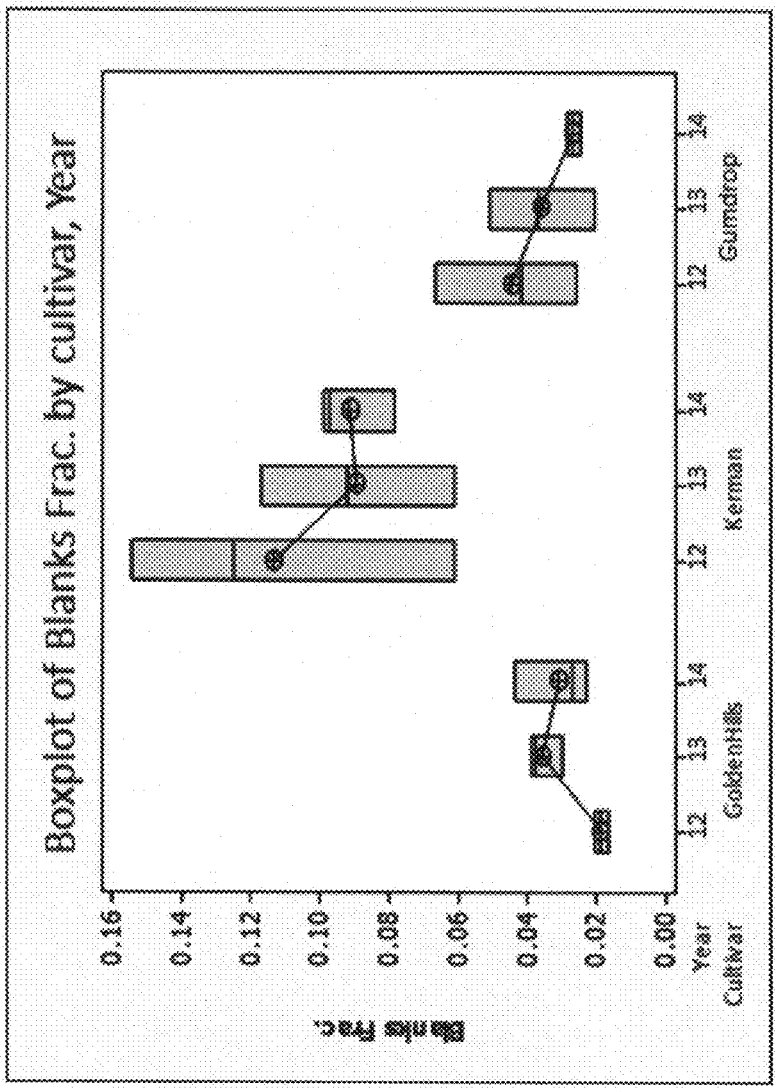
FIG. 4A illustrates fraction of blank nuts for 'Golden Hills', 'Kerman', and 'Gumdrop' over several years (Years 12-14).

Nut Characteristics, Blank nuts: Based on data from Years 12-14, 'Gumdrop' had a low level of blank nuts (fully formed shell but no kernel). Growers are not paid for blanks. Some genotypes have naturally high levels of blanks and give the impression of high yield prior to harvest. 'Gumdrop' was similar (3.6%) to 'Golden Hills' (2.9%) but significantly less (Bonferroni, Tukey tests) than 'Kerman' (9.8%) (FIG. 4A).

Figure 4B:
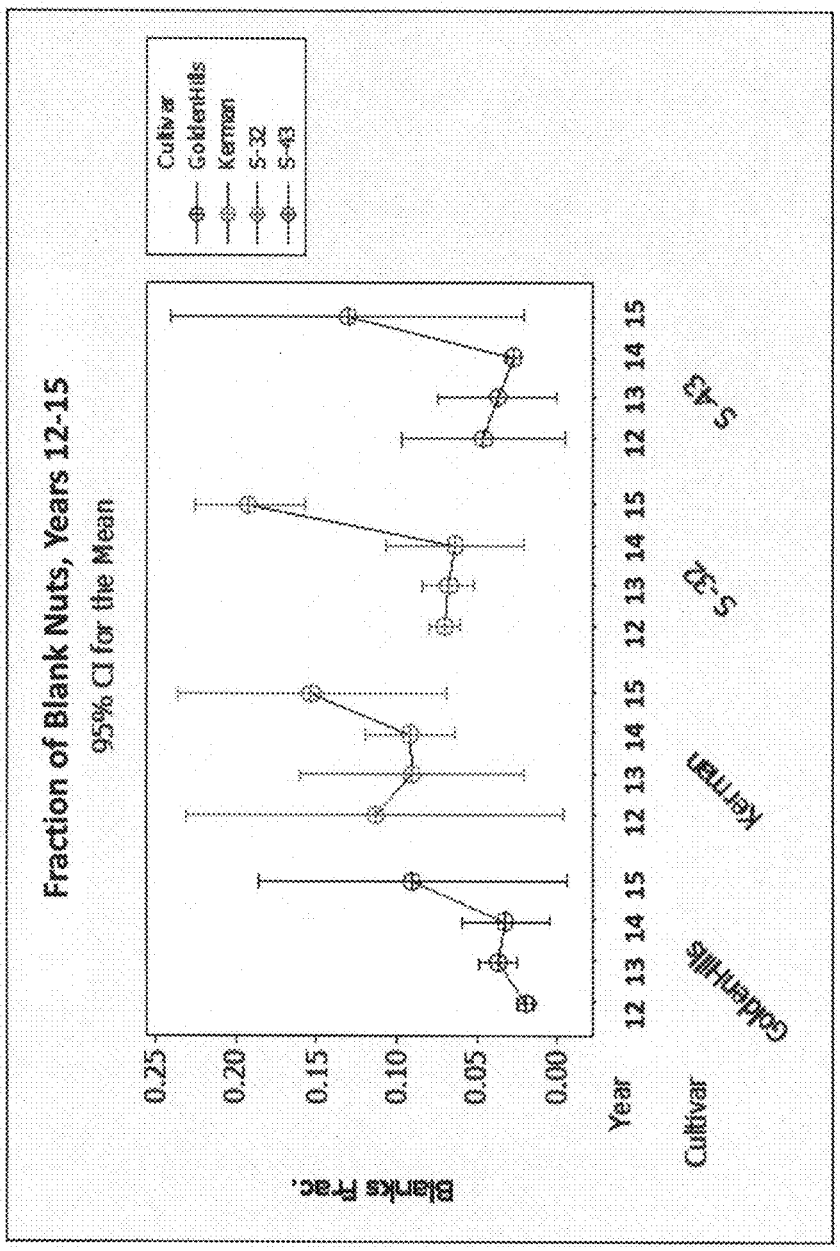
FIG. 4B illustrates fraction of blank nuts for 'Golden Hills', 'Kerman', 'Gumdrop' ('S-43'), and 'S-32' over several years (Years 12-15).
Figure 4C:
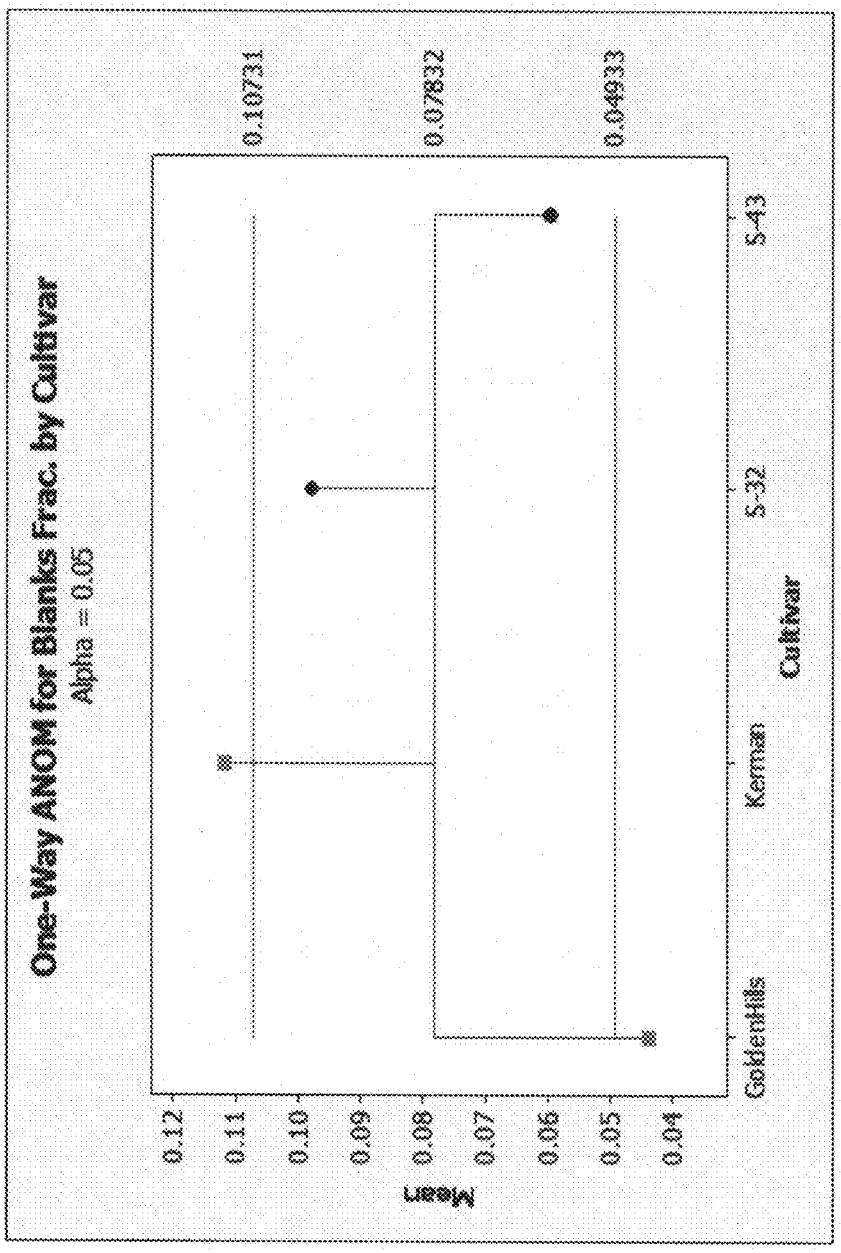
FIG. 4C illustrates an analysis of means for blank nut fraction for 'Golden Hills', 'Kerman', 'Gumdrop' ('S-43'), and 'S-32' over several years (Years 12-15). 'Gumdrop' trees were 5 years old in Year 12.

Year 15 was an exceptional year and all of the tested cultivars had unusually high blank percentages ('Kerman'=15.3%, 'Golden Hills'=8.9%, 'S-43'=13.0%). 'Gumdrop' had a low level of blank nuts from Years 12-14 (3.6%), similar to 'Golden Hills' (2.9%) but significantly less (Bonferroni) than 'Kerman' (9.8%). An analysis and statistics summary is provided in Table 6A and Table 6B. 'Kerman' has a reputation for producing blanks, and over the 4 years of data collection (Years 12-15), averaged 11.2%. Across all 4 years of the trial (Years 12-15), 'Gumdrop' had significantly fewer blanks than 'Kerman' (5.97% vs. 11.2%), and similar values to 'Golden Hills' (4.4%) (FIG. 4B and FIG. 4C).

TABLE 6A

Analysis of Variance for Blanks Fraction

| Source | DF | MS | F | P |
|---|---|---|---|---|
| Cultivar | 3 | 0.0121874 | 23.83 | 0.000 |
| Year | 3 | 0.0210644 | 41.19 | 0.000 |
| Cultivar*Year | 9 | 0.0009813 | 1.92 | 0.087 |
| Block | 2 | 0.0014740 | 2.88 | 0.072 |
| Error | 30 | 0.0005113 | | |
| Total | 47 | | | |

S = 0.0226130
R-Sq = 87.91%
R-Sq(adj) = 81.06%

TABLE 6B

Mean differences for blank fractions (lower diagonal) and P values (upper diagonal) for Bonferroni pairwise comparisons

| | Golden Hills | Kerman | S-32 | S-43 |
|---|---|---|---|---|
| Golden Hills | — | 0.0000 | 0.0000 | 0.5749 |
| Kerman | 0.068 | — | 0.8780 | 0.0000 |
| S-32 | 0.054 | −0.014 | — | 0.0015 |
| S-43 (Gumdrop) | 0.016 | −0.052 | −0.038 | — |

Figure 5A:
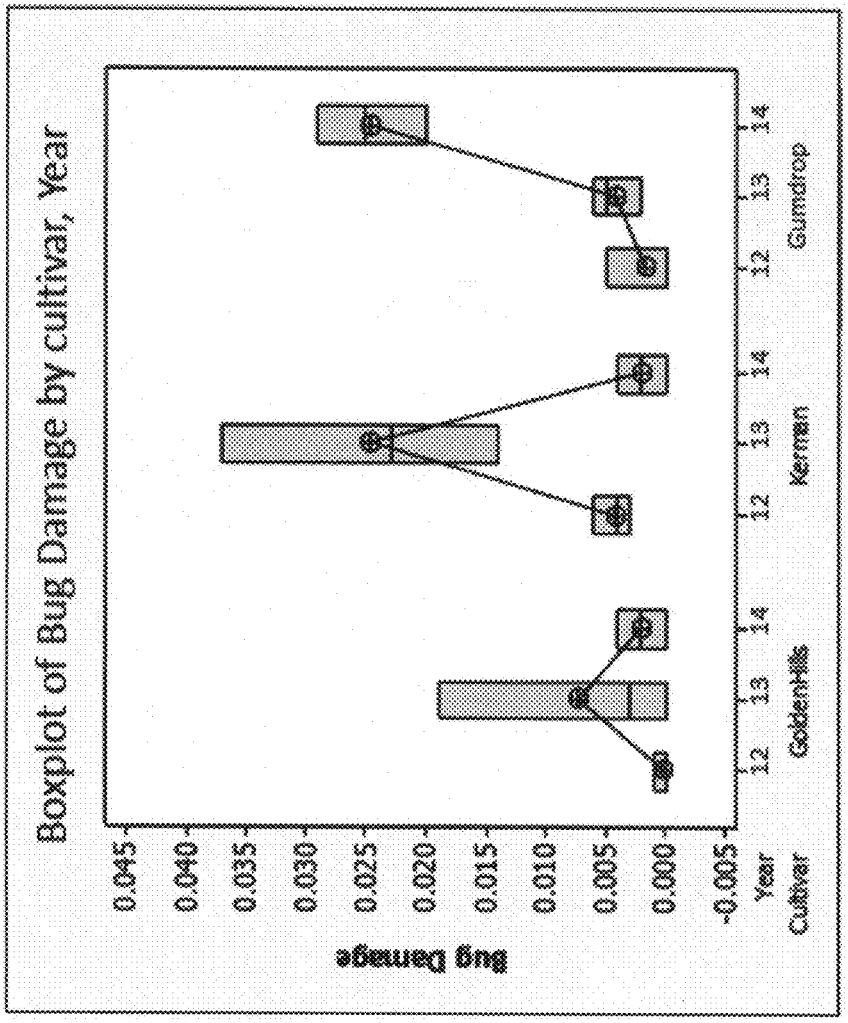
FIG. 5A illustrates bug damage for 'Golden Hills', 'Kerman', and 'Gumdrop' over several years (Years 12-14).

Nut Characteristics, Insect damaged nuts: Insect damaged nuts are considered a defect. Insect damage was generally very low in the plot analyzed (0.5%), except for Year 13, when 'Golden Hills' and 'Kerman' had significant damage (>2.0%). Overall, insect damage for 'Gumdrop' was not significantly different among cultivars (GLM ANOVA), but year by cultivar (year*cultivar) interactions were significantly different based on the analysis for Years 12-14 (FIG. 5A). 'Gumdrop' had low insect damage in Year 13, but high levels in Year 14. This discrepancy may be due to differences in harvest date among the cultivars and/or different types of insect activity during the pre-harvest period.

Figure 5B:
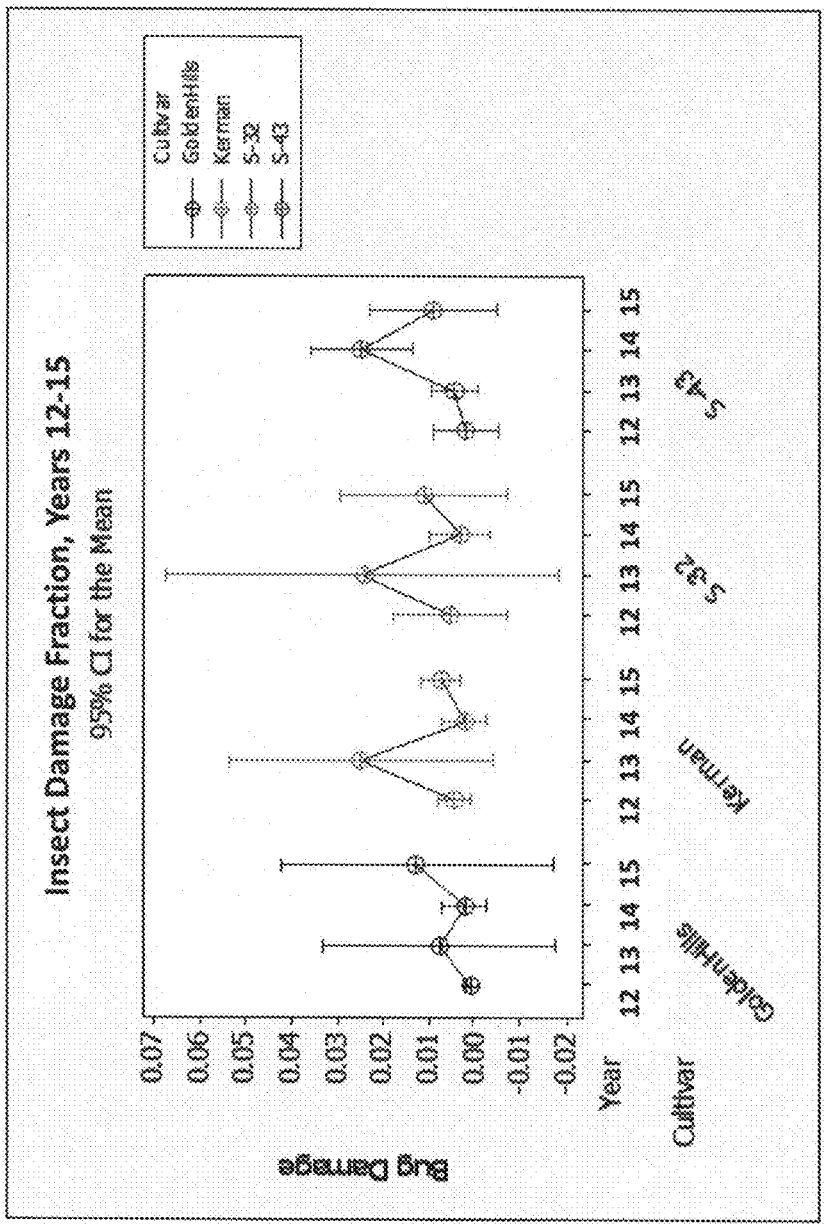
FIG. 5B illustrates insect damage fraction for 'Golden Hills', 'Kerman', 'Gumdrop' ('S-43'), and 'S-32' over several years (Years 12-15).
Figure 5C:
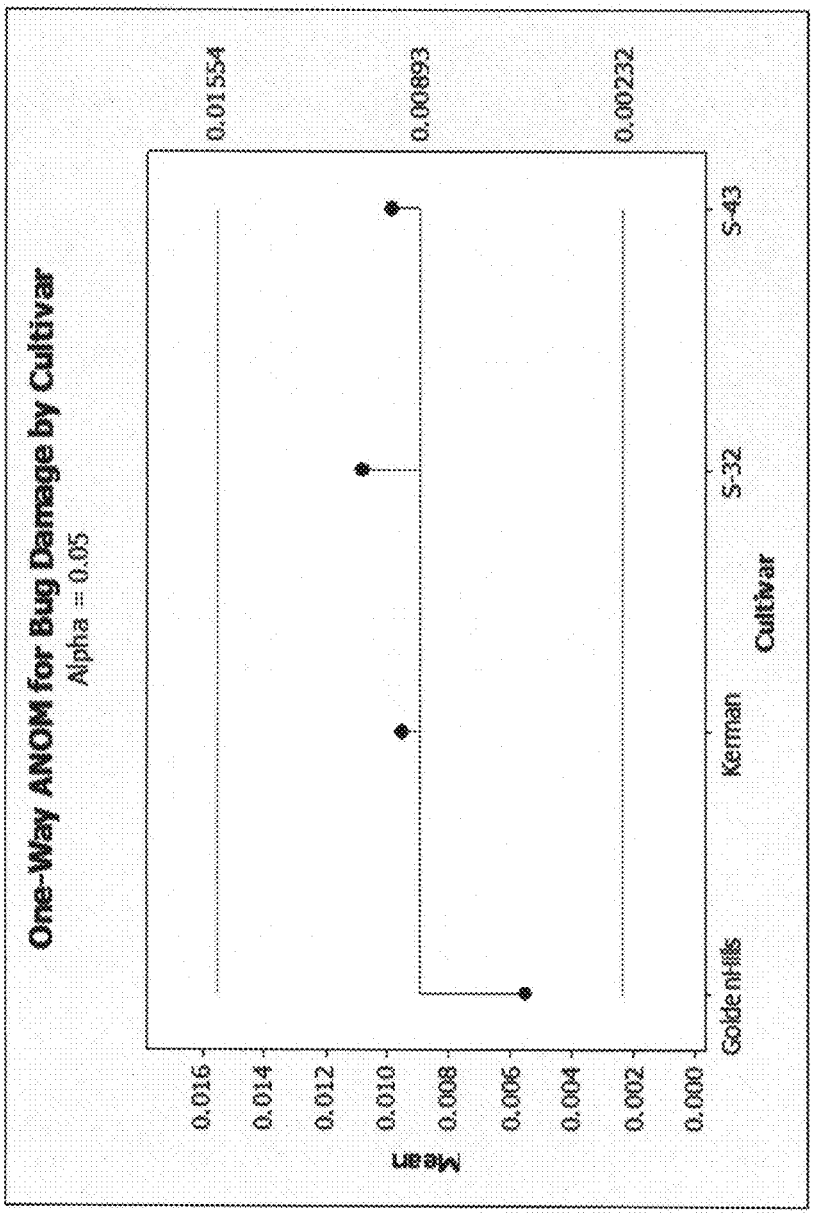
FIG. 5C illustrates an analysis of means for insect damage for 'Golden Hills', 'Kerman', 'Gumdrop' ('S-43'), and 'S-32' over several years (Years 12-15). 'Gumdrop' trees were 5 years old in Year 12.

The combined data for Years 12-15 were also analyzed. Insect damage remained very low in the plot analyzed (0.9%), even through Year 15, again with the exception of Year 13 as described above (FIG. 5B and FIG. 5C). 'Golden Hills' also had relatively high levels of insect damage in Year 15. Overall, insect damage was not significantly different among cultivars, but cultivar by year (cultivar*year) interactions were significantly different. Analysis summaries are provided in Table 7A and Table 7B. 'Gumdrop' had low insect damage in Year 13, but somewhat higher levels in both Year 14 and Year 15. The harvest of 'Gumdrop' was delayed again in Year 15, as was also the case in past years, because no processor was available at the early date of 'Gumdrop' maturity to process the nuts. A timely harvest is likely to reduce insect damage and shell staining. Ensuring a timely harvest is likely to reduce the degree of insect damage and shell staining. The nuts in this trial (and the whole orchard) were not treated for Navel Orangeworm due to poor yields of 'Kerman' in the oil-treated portion of the block in Year 15. The trial area was not oiled in its entirety.

TABLE 7A

Analysis of Variance for Insect Damage

| Source | DF | MS | F | P |
|---|---|---|---|---|
| Cultivar | 3 | 0.0000661 | 1.29 | 0.294 |
| Year | 3 | 0.0003113 | 6.09 | 0.002 |
| Cultivar*Year | 9 | 0.0002306 | 4.51 | 0.001 |
| Block | 2 | 0.0000775 | 1.52 | 0.236 |
| Error | 30 | 0.0000511 | | |
| Total | 47 | | | |

S = 0.00714777
R-Sq = 68.69%
R-Sq(adj) = 50.95%

TABLE 7B

Mean differences for insect damage fractions (lower diagonal) and P values (upper diagonal) for Bonferroni pairwise comparisons

| | Golden Hills | Kerman | S-32 | S-43 |
|---|---|---|---|---|
| Golden Hills | — | 1.0000 | 0.4755 | 0.8607 |
| Kerman | 0.004 | — | 1.0000 | 1.0000 |
| 5-32 | 0.005 | 0.001 | — | 1.0000 |
| 5-43 (Gumdrop) | 0.004 | 0.0004 | −0.001 | — |

'Gumdrop' has not been specifically evaluated for resistance or susceptibility to pistachio diseases. This variety is grown in a location where typical pistachio diseases are minimal, and which is managed to minimize disease development. It is expected that susceptibility to *Botryosphaeria dothidea, Botrytis cinerea,* or *Alternaria alternata* would be similar to other commercial pistachio cultivars since *Pistacia vera* L. in California is generally susceptible to these diseases. Most pistachio insect pests are controlled with insecticides, which have been used where 'Gumdrop' is grown. Significant differences in unspecified insect damage were not found among the tested cultivars, including 'Gumdrop'. However, work with 'Golden Hills' has shown that lower incidence of Navel Orangeworm is present when the nuts can be harvested earlier in the season. 'Gumdrop' matures much earlier than 'Golden Hills', and therefore would be expected to be exposed to fewer Navel Orangeworm attacks.

Figure 6A:
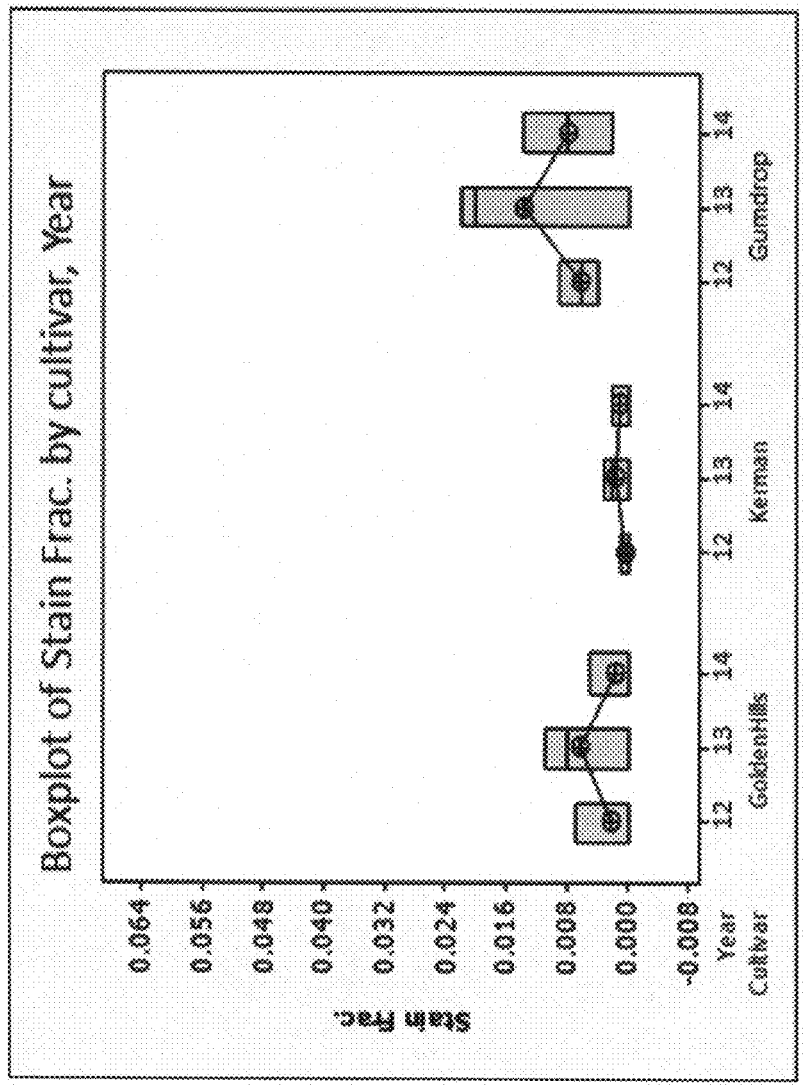
FIG. 6A illustrates stain fraction for 'Golden Hills', 'Kerman', and 'Gumdrop' over several years (Years 12-14).
Figure 6B:
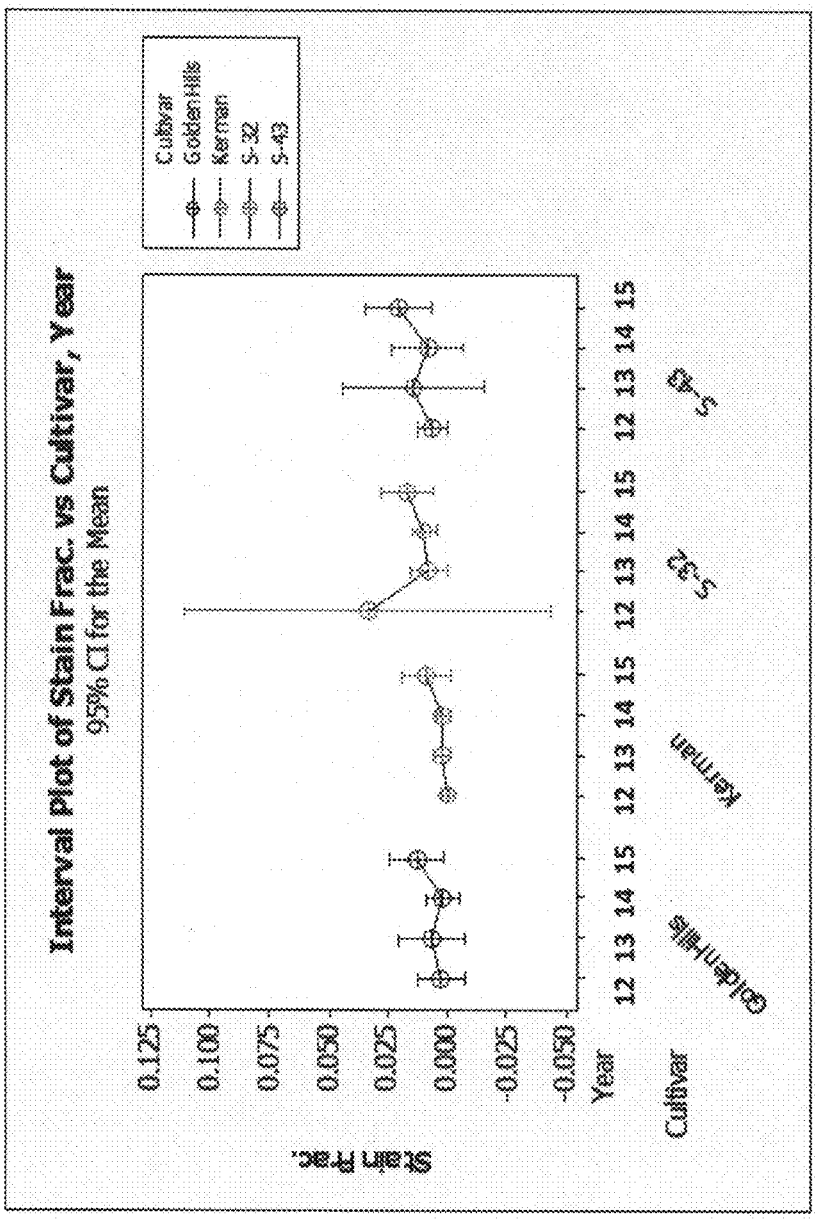
FIG. 6B illustrates stain fraction for 'Golden Hills', 'Kerman', 'Gumdrop' ('S-43'), and 'S-32' over several years (Years 12-15).
Figure 6C:
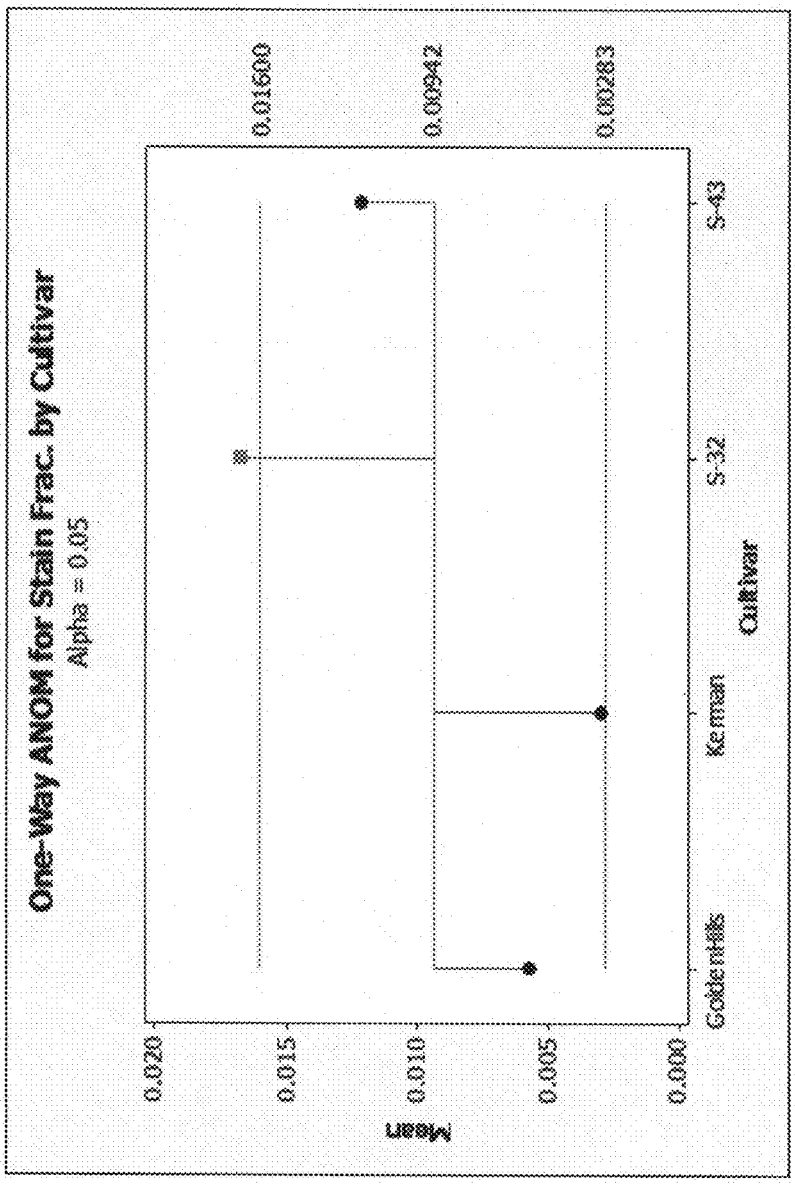
FIG. 6C illustrates an analysis of means for stain fraction for 'Golden Hills', 'Kerman', 'Gumdrop' ('S-43'), and 'S-32' over several years (Years 12-15). 'Gumdrop' trees were 5 years old in Year 12.
Figure 11A:
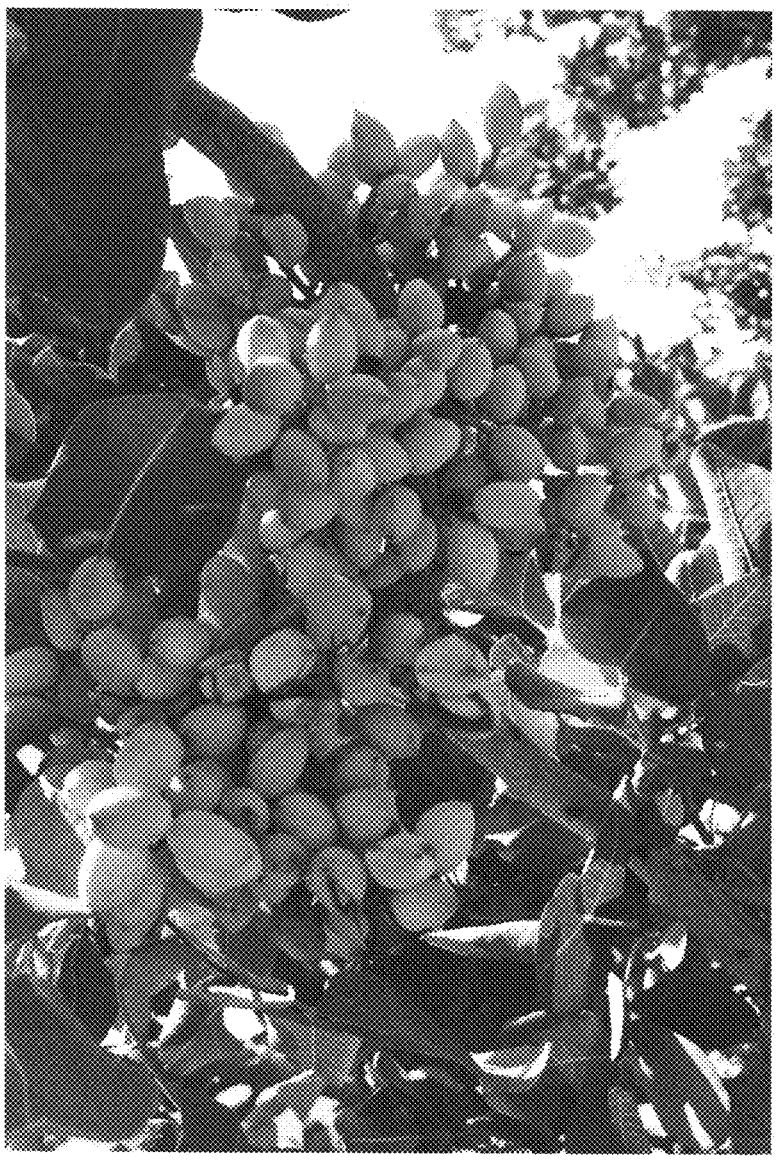
FIG. 11A illustrates nut clusters at maturity on 8-year-old 'Gumdrop' trees, showing the general size and shape of the clusters (e.g. number of nuts and distribution in the clusters).
Figure 11B:
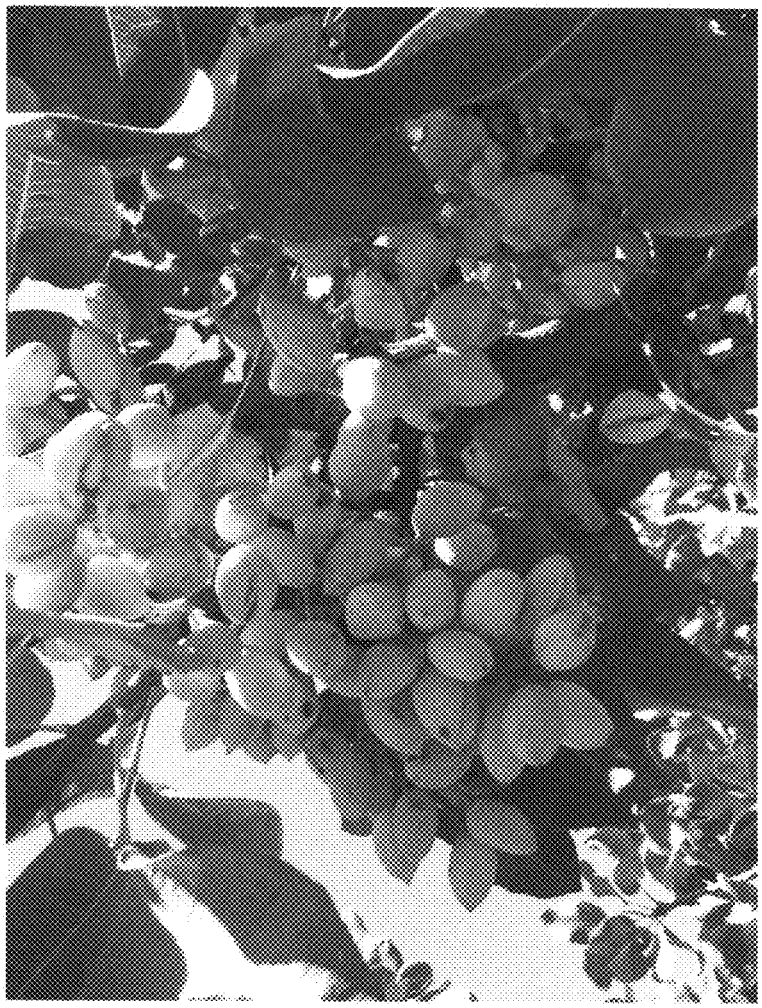
FIG. 11B illustrates an additional view of 'Gumdrop' nut clusters.
Figure 11C:
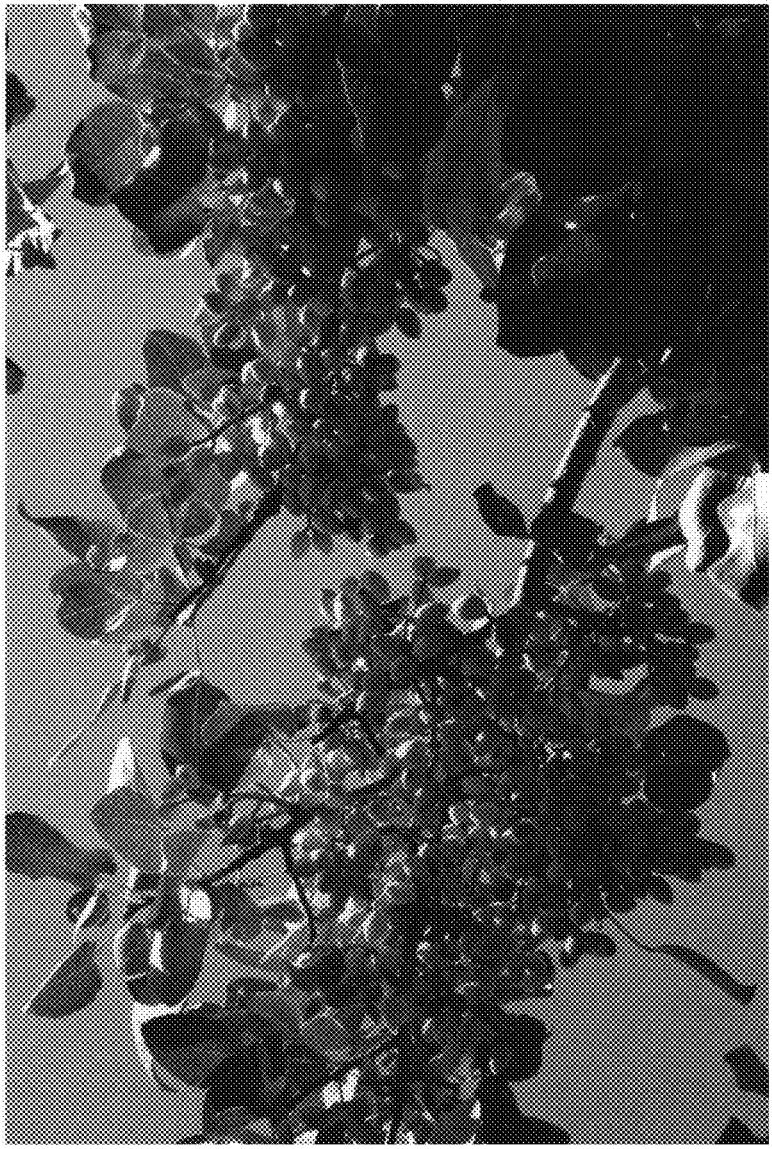
FIG. 11C illustrates nut clusters at maturity on 10-year-old 'Gumdrop' trees.
Figure 12A:
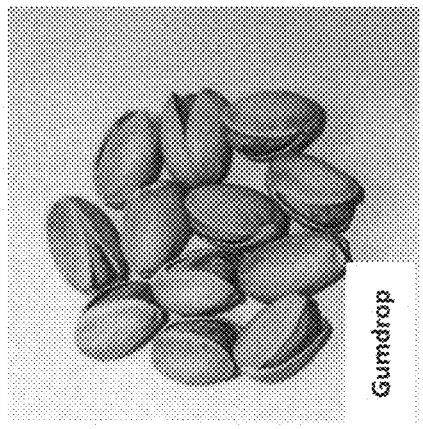
FIG. 12A, FIG. 12B, and FIG. 12C illustrate the appearance of husked and dried nuts from 8-year-old 'Gumdrop' trees (FIG. 12A), 'Kerman' (FIG. 12B), and 'Golden Hills' (FIG. 12C).

Nut Characteristics, Shell staining: Shell staining is an important characteristic, impacting consumer acceptance. Shell staining is the reason, along with bug damage, that Iranian pistachio cultivars were stained red—to cover the defect. For Years 12-14, shell staining was minimal for all of the cultivars, except for 'S-32' in the first harvest year (Year 12). 'Gumdrop' had somewhat higher (non-significant by Bonferroni, Tukey tests) stain fraction (0.9%) than 'Kerman' (0.1%) or 'Golden Hills' (0.3%) (FIG. 6A and FIG. 12A). For Years 12-15, 'Gumdrop' had somewhat higher (non-significant by Bonferroni) stain fraction (1.22%) than 'Kerman' (0.30%) or 'Golden Hills' (0.575%) (FIG. 6B and FIG. 6C). An analysis and statistics summary is provided in Table 8A and Table 8B. Views of the 'Gumdrop' nut clusters at maturity are presented in FIG. 11A. FIG. 11B and FIG. 11C illustrate additional views of 'Gumdrop' nut clusters.

TABLE 8A

Analysis of Variance for Stain Fraction

| Source | DF | MS | F | P |
|---|---|---|---|---|
| Cultivar | 3 | 0.0004638 | 5.86 | 0.003 |
| Year | 3 | 0.0002033 | 2.57 | 0.073 |
| Cultivar*Year | 9 | 0.0001503 | 1.90 | 0.091 |
| Block | 2 | 0.0001626 | 2.05 | 0.146 |
| Error | 30 | 0.0000792 | | |
| Total | 47 | | | |

S = 0.00889975
R-Sq = 60.76%
R-Sq(adj) = 38.53%

TABLE 8B

Mean differences for stain fractions (lower diagonal) and P values (upper diagonal) for Bonferroni pairwise comparisons

| | Golden Hills | Kerman | 5-32 | 5-43 |
|---|---|---|---|---|
| Golden Hills | — | 1.0000 | 0.0302 | 0.5254 |
| Kerman | −0.003 | — | 0.0041 | 0.1030 |
| 5-32 | 0.011 | 0.014 | — | 1.0000 |
| 5-43 (Gumdrop) | 0.006 | 0.009 | −0.004 | — |

Figure 7A:
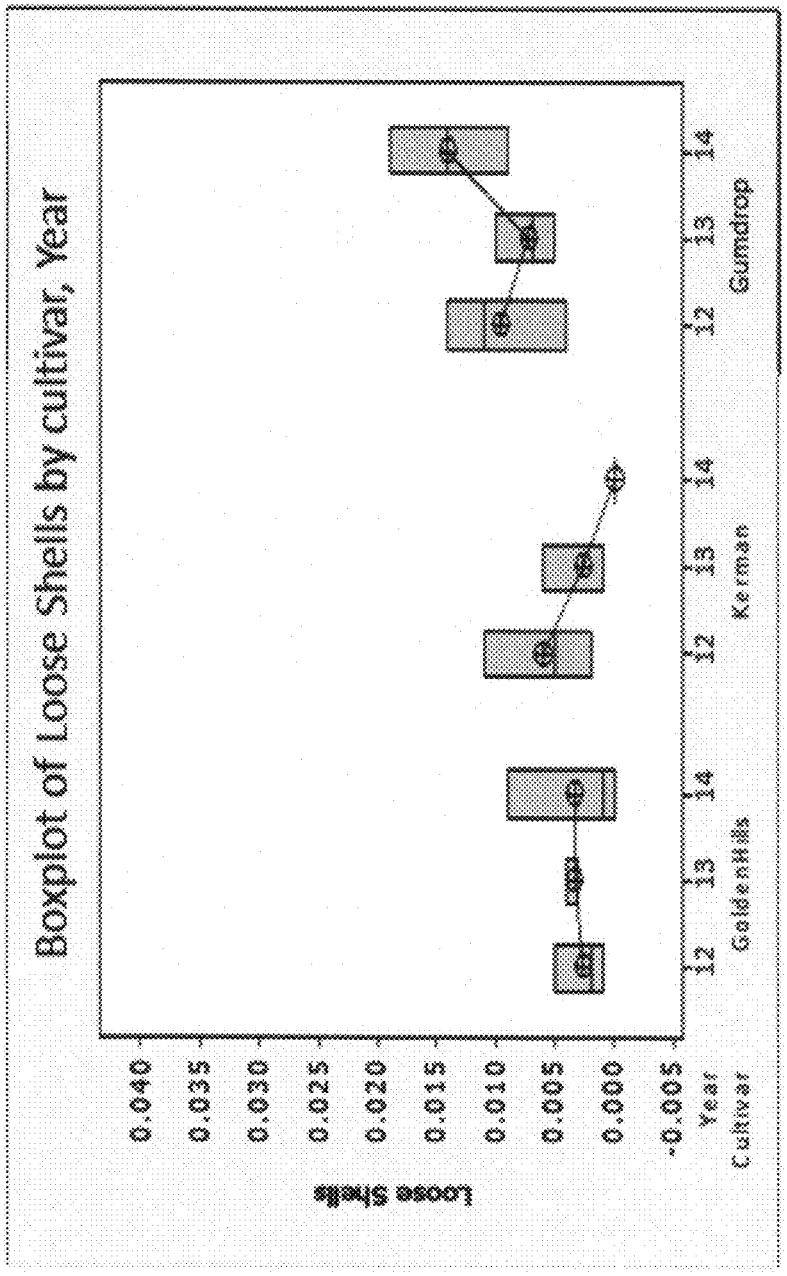
FIG. 7A illustrates loose shells for 'Golden Hills', 'Kerman', and 'Gumdrop' over several years (Years 12-14).
Figure 7B:
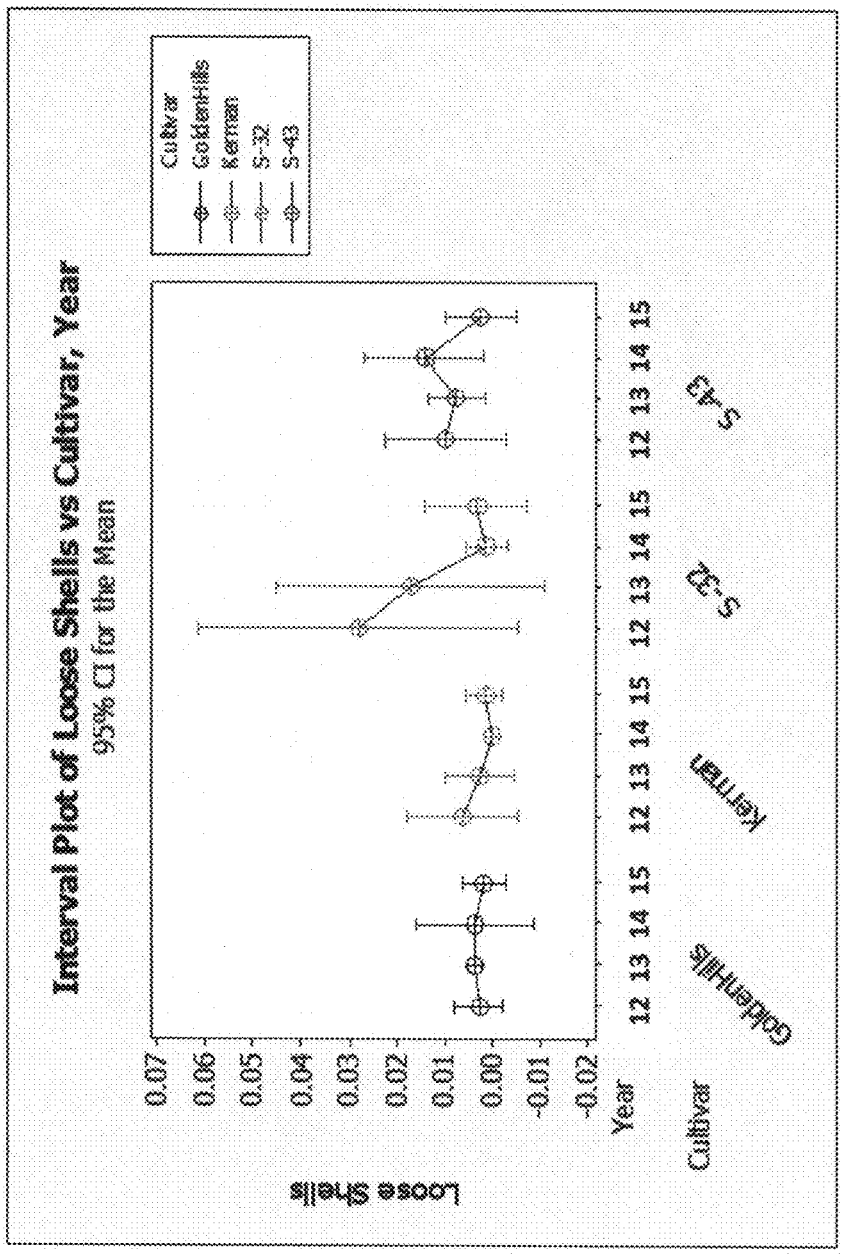
FIG. 7B illustrates loose shells for 'Golden Hills', 'Kerman', 'Gumdrop' ('S-43'), and 'S-32' over several years (Years 12-15).
Figure 7C:
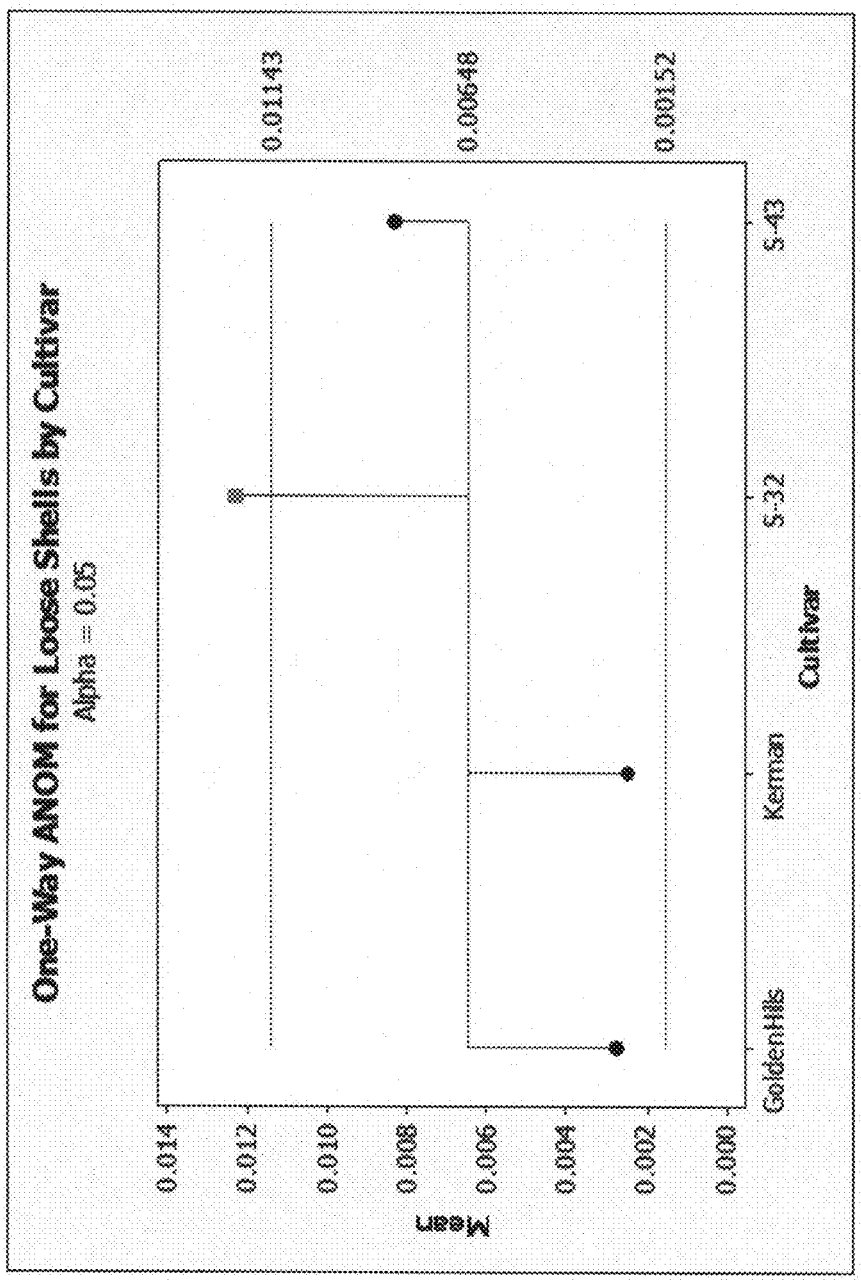
FIG. 7C illustrates an analysis of means for loose shells for 'Golden Hills', 'Kerman', 'Gumdrop' ('S-43'), and 'S-32' over several years (Years 12-15). 'Gumdrop' trees were 5 years old in Year 12.
Figure 12B:
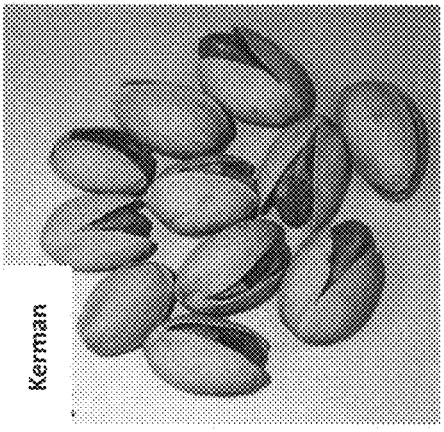
Figure 12C:
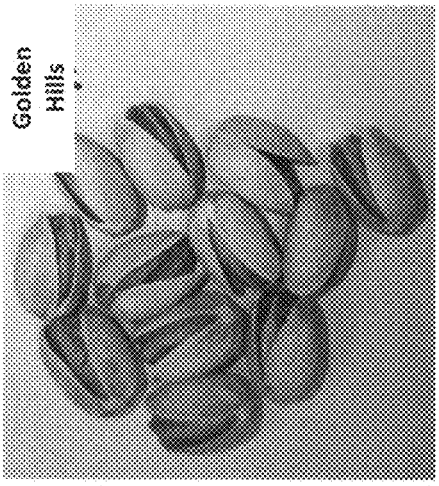

Nut Characteristics, loose shells: The loose shell evaluation measures the tendency of the husked nuts to lose their shells during or after processing, resulting in loose kernels and shell pieces in the commercial in-shell product stream. Loose shells are a function of shell hinge strength. If hinge strength is exceptionally high (no loose shells), consumers will have difficulty extracting the nuts from the shells. For this reason, hinge strength should be at an intermediate level, rather than extremely strong or weak. For Years 12-14, 'Gumdrop' had higher, but non-significantly different (Bonferroni, Tukey tests), levels (1.0%) of loose shells than 'Kerman' (0.3%) or 'Golden Hills' (0.3%) (FIG. 7A). For Years 12-15, 'Gumdrop' had higher, but non-significantly different (Bonferroni test), levels (0.84%) of loose shells than 'Kerman' (0.25%) or 'Golden Hills' (0.28%) (FIG. 7B and FIG. 7C). An analysis and statistics summary is provided in Table 9A and Table 9B. The appearance of husked and dried nuts of 'Gumdrop', 'Kerman', and 'Golden Hills' are presented in FIG. 12A, FIG. 12B, and FIG. 12C, respectively.

TABLE 9A

Analysis of Variance for Loose Shells

| Source | DF | MS | F | P |
|---|---|---|---|---|
| Cultivar | 3 | 0.0002694 | 9.11 | 0.000 |
| Year | 3 | 0.0001984 | 6.71 | 0.001 |
| Cultivar*Year | 9 | 0.0001239 | 4.19 | 0.001 |

TABLE 9A-continued

Analysis of Variance for Loose Shells

| Source | DF | MS | F | P |
|---|---|---|---|---|
| Block | 2 | 0.0000204 | 0.69 | 0.510 |
| Error | 30 | 0.0000296 | | |
| Total | 47 | | | |

S = 0.00543707
R-Sq = 74.27%
R-Sq(adj) = 59.69%

TABLE 9B

Mean differences for loose shell fractions (lower diagonal) and P values (upper diagonal) for Bonferroni pairwise comparisons

| | Golden Hills | Kerman | S-32 | S-43 |
|---|---|---|---|---|
| Golden Hills | — | 1.0000 | 0.0010 | 0.1013 |
| Kerman | −0.0003 | — | 0.0007 | 0.0762 |
| 5-32 | 0.0096 | 0.0098 | — | 0.5184 |
| S-43 (Gumdrop) | 0.0056 | 0.0059 | −0.0040 | — |

Figure 8A:
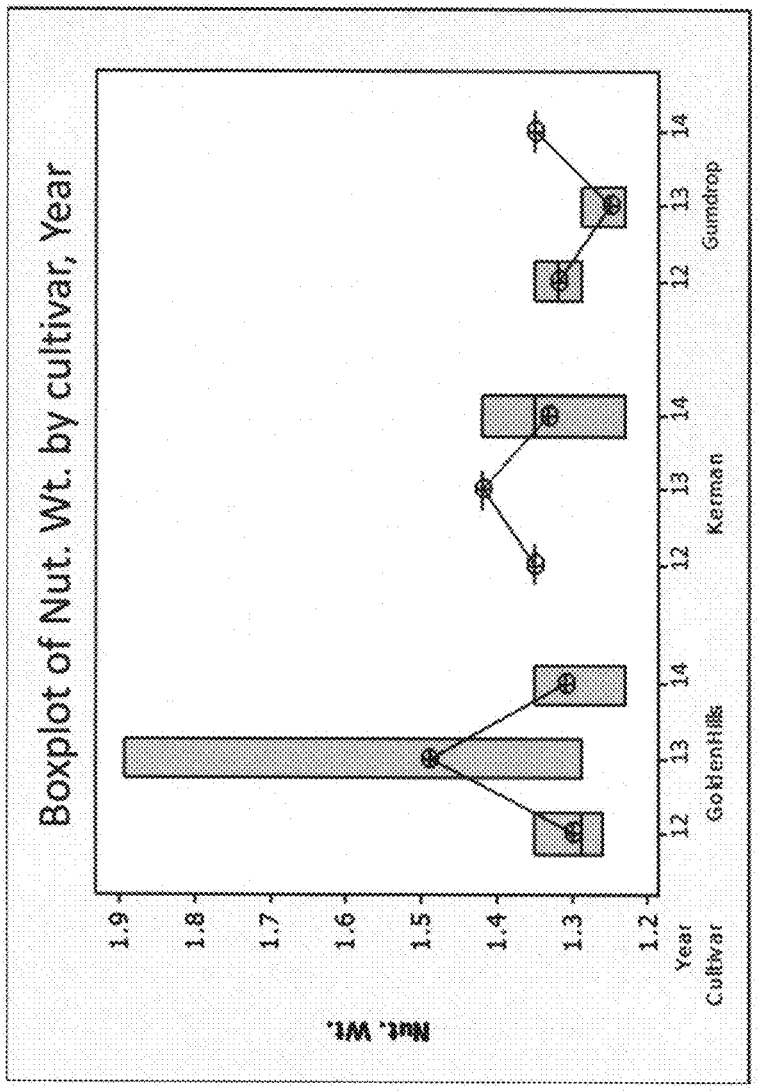
FIG. 8A illustrates nut weight for 'Golden Hills', 'Kerman', and 'Gumdrop' over several years (Years 12-14).
Figure 13:
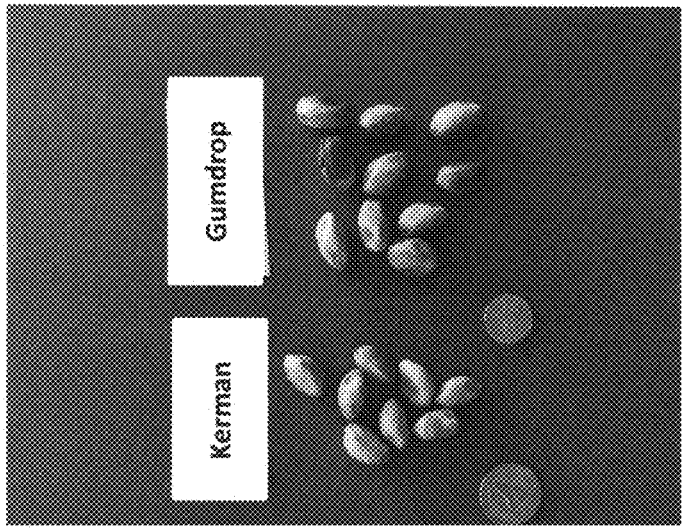
FIG. 13 illustrates the relative size and appearance of isolated kernels from 8-year-old 'Gumdrop' and 'Kerman' trees.

Nut Characteristics, nut weight (including shells), and nut quality: Nut weight, nut length, and nut width are correlated characters, so only nut weight as a measure of nut size is presented in the analysis for Years 12-14. Nut size was generally similar for all of the cultivars and years, except for 'Golden Hills' in harvest year 2 (Year 13). 'Gumdrop' had a mean nut weight of 1.31 g, and both 'Kerman' and 'Golden Hills' had a mean nut weight of 1.37 g (FIG. 8A). Cultivar and Year effects were not significantly different (ANOVA, Bonferroni, Tukey tests). Nut quality for 'Gumdrop' is similar to other cultivars, with the exception that the husks tend to be 'gummy' or sticky. However, processers have not indicated that this is a problem after processing, and the processed nuts for 'Gumdrop' are similar in appearance to 'Kerman' or 'Golden Hills'. Views of isolated nut kernels from 'Gumdrop' and 'Kerman' are presented in FIG. 13.

Figure 8B:
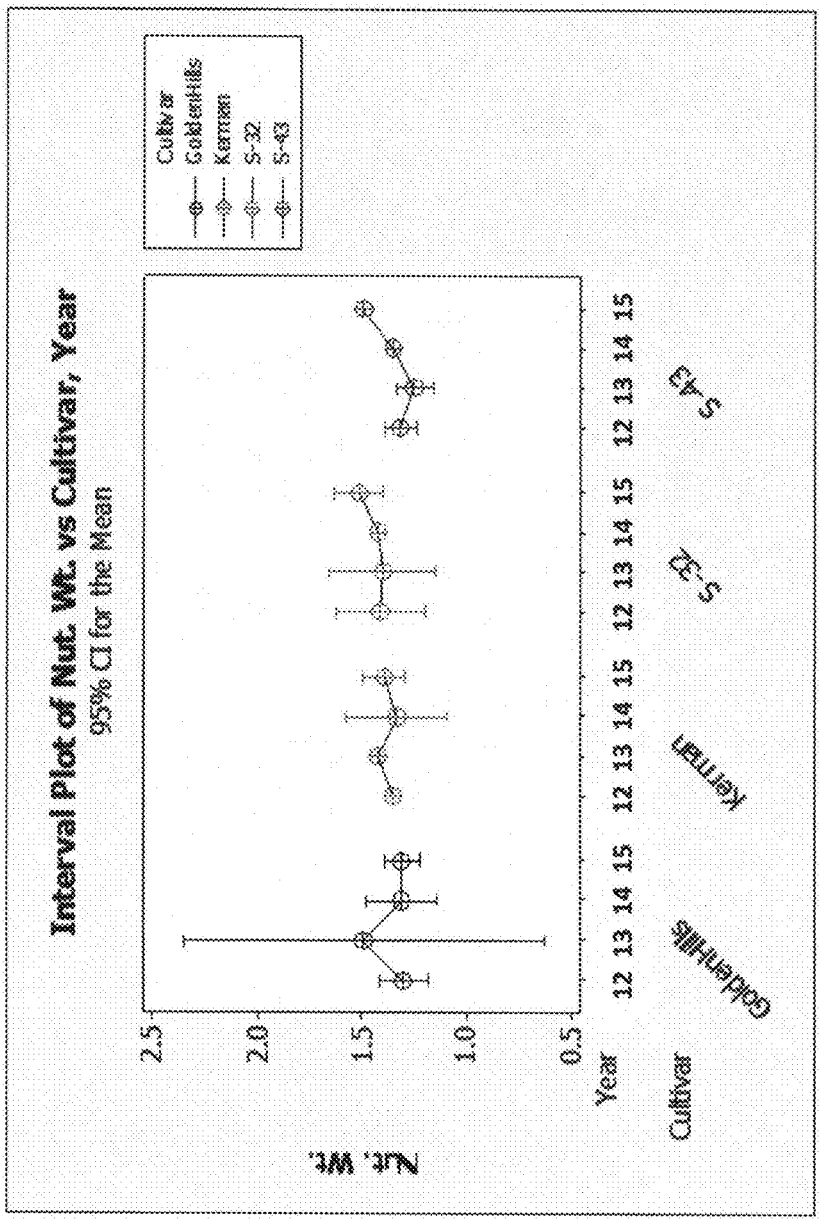
FIG. 8B illustrates nut weight for 'Golden Hills', 'Kerman', 'Gumdrop' ('S-43'), and 'S-32' over several years (Years 12-15).
Figure 8C:
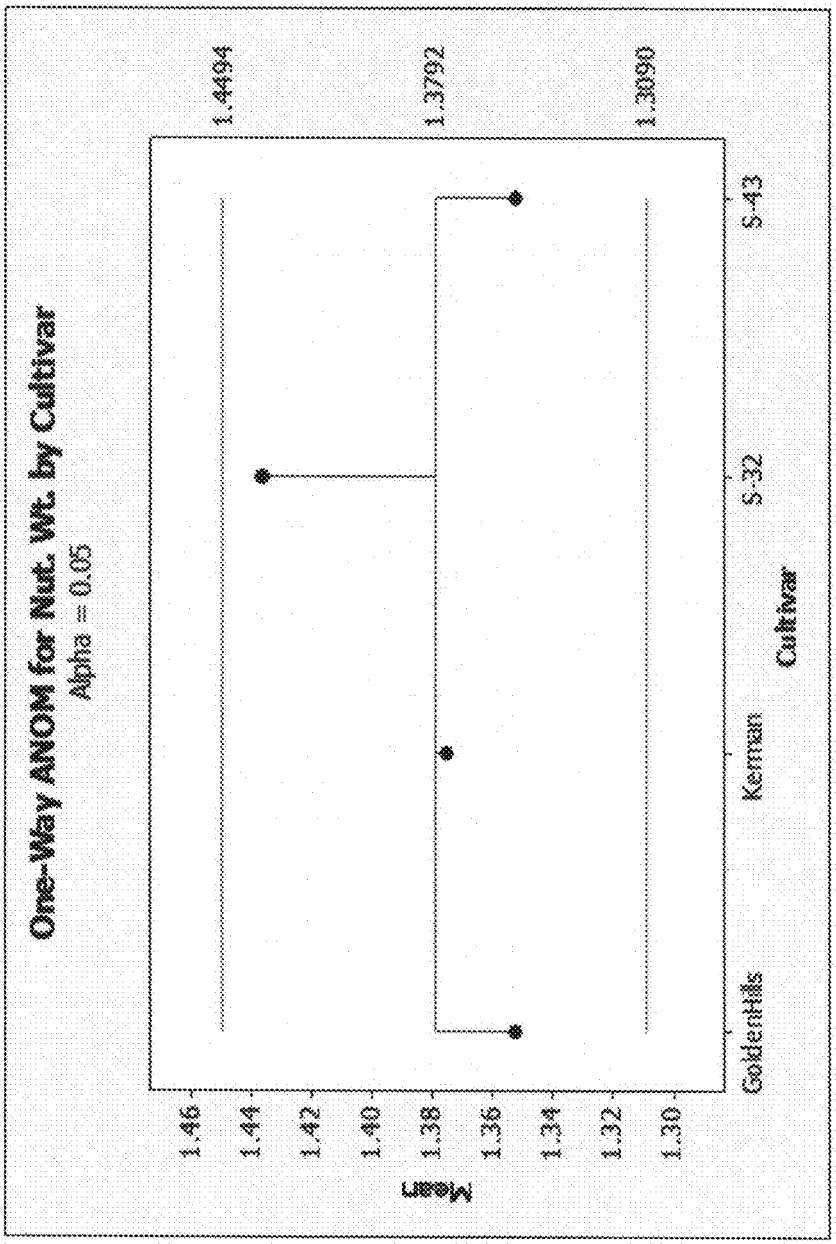
FIG. 8C illustrates an analysis of means for nut weight for 'Golden Hills', 'Kerman', 'Gumdrop' ('S-43'), and 'S-32' over several years (Years 12-15). 'Gumdrop' trees were 5 years old in Year 12.

The combined data for Years 12-15 were also analyzed. 'Gumdrop' had a mean nut weight of 1.35 g, 'Kerman' had a mean nut weight of 1.38 g, and 'Golden Hills' had a mean nut weight of 1.35 g (FIG. 8B and FIG. 8C). Cultivar and Year effects were not significantly different (by ANOVA, ANOMA, and Bonferroni paired comparisons). An analysis and statistics summary is provided in Table 10A and Table 10B.

TABLE 10A

Analysis of Variance for Nut Weight

| Source | DF | MS | F | P |
|---|---|---|---|---|
| Cultivar | 3 | 0.01898 | 1.85 | 0.160 |
| Year | 3 | 0.01748 | 1.70 | 0.188 |
| Cultivar*Year | 9 | 0.01729 | 1.68 | 0.137 |
| Block | 2 | 0.00661 | 0.64 | 0.533 |
| Error | 30 | 0.01028 | | |
| Total | 47 | | | |

TABLE 10B

Mean differences for nut weight in grams (lower diagonal) and P values (upper diagonal) for Bonferroni pairwise comparisons

| | Golden Hills | Kerman | S-32 | S-43 |
|---|---|---|---|---|
| Golden Hills | — | 1.0000 | 0.3056 | 1.0000 |
| Kerman | 0.0225 | — | 0.8802 | 1.0000 |
| 5-32 | 0.0842 | 0.0617 | — | 0.5184 |
| S-43 (Gumdrop) | 0.0000 | −0.0225 | −0.0842 | — |

Figure 14A:
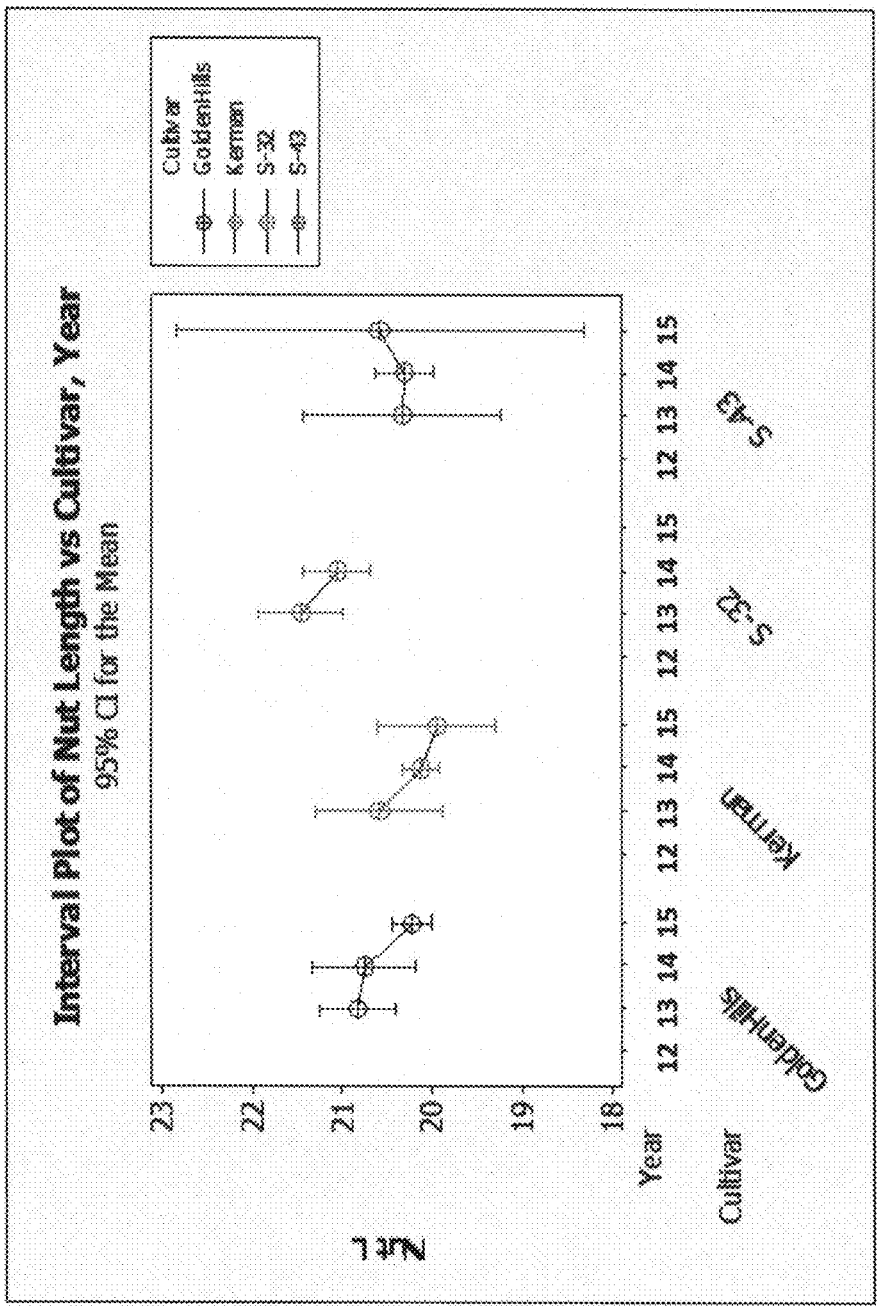
FIG. 14A illustrates nut length (mm) for 'Golden Hills', 'Kerman', 'Gumdrop' ('S-43'), and 'S-32' over several years (Years 13-15).
Figure 14B:
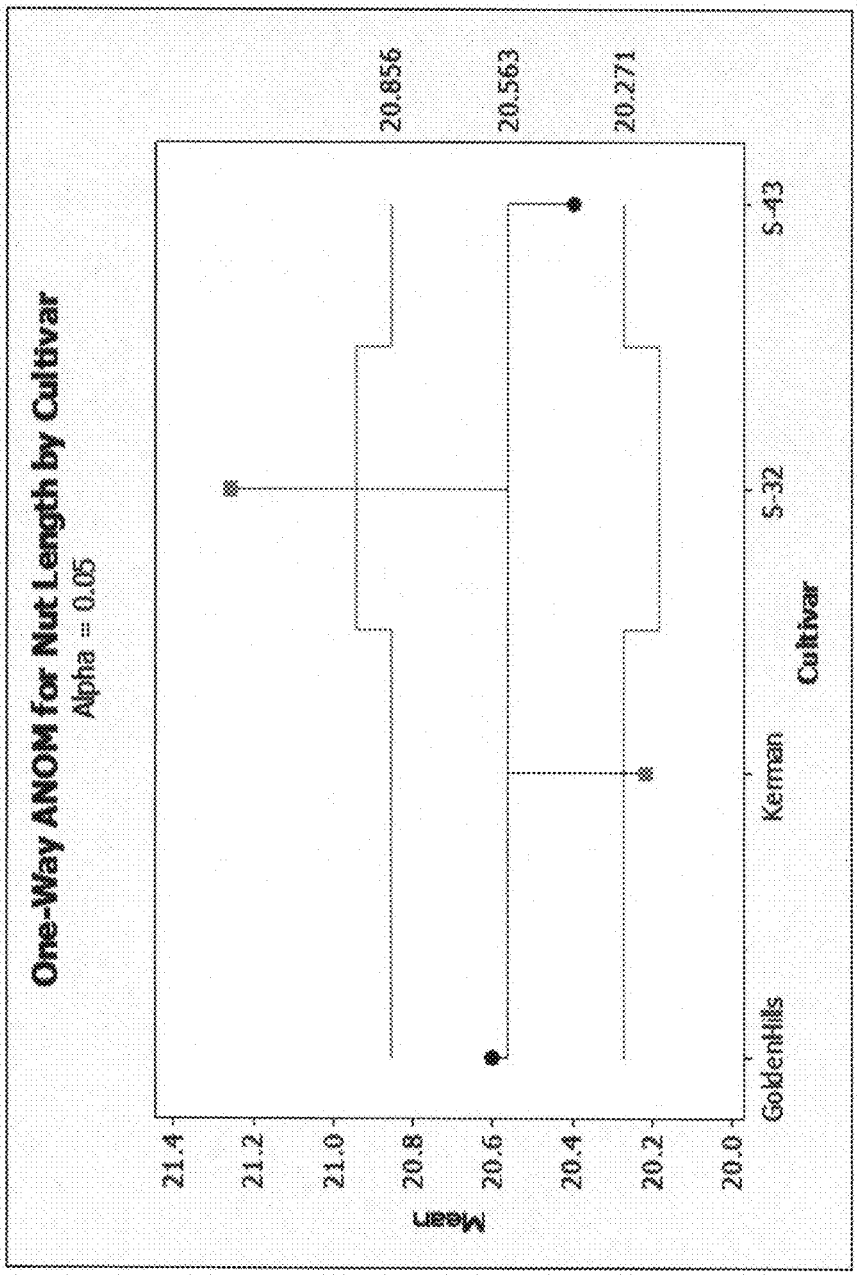
FIG. 14B illustrates an analysis of means for nut length (mm) for 'Golden Hills', 'Kerman', 'Gumdrop' ('S-43'), and 'S-32' over several years (Years 13-15). 'Gumdrop' trees were 6 years old in Year 13.

Nut Characteristics: nut length and nut width: Two parameters were measured from Year 13-Year 15: nut length and nut width (measured parallel to the split). Nut length values for 'Gumdrop' ('S-43'), 'Golden Hills', and 'Kerman' were not significantly different (20.4 mm, 20.6 mm, and 20.22 mm, respectively) (FIG. 14A and FIG. 14B). 'Gumdrop' was intermediate in terms of nut length between 'Kerman' and 'Golden Hills', having a nut length difference of ~0.2 mm from each of them. An analysis and statistics summary is provided in Table 11A and Table 11B.

TABLE 11A

Analysis of Variance for Nut Length

| Source | DF | Adj MS | F | P |
|---|---|---|---|---|
| Cultivar | 3 | 1.1294 | 8.20 | 0.001 |
| Year | 2 | 0.3323 | 2.41 | 0.110 |
| Block | 2 | 0.1232 | 0.89 | 0.422 |
| Error | 25 | 3.4452 | 0.1378 | |
| Total | 32 | | | |

S = 0.371226
R-Sq = 59.97%
R-Sq(adj) = 48.76%

TABLE 11B

Mean differences for nut length (lower diagonal) and P values (upper diagonal) for Bonferroni pairwise comparisons

| | Golden Hills | Kerman | S-32 | S-43 |
|---|---|---|---|---|
| Golden Hills | — | 0.2191 | 0.0498 | 1.0000 |
| Kerman | −0.387 | — | 0.0004 | 1.0000 |

TABLE 11B-continued

Mean differences for nut length (lower diagonal) and P values (upper diagonal) for Bonferroni pairwise comparisons

| | Golden Hills | Kerman | S-32 | S-43 |
|---|---|---|---|---|
| S-32 | 0.579 | 0.966 | — | 0.004 |
| S-43 (Gumdrop) | 0.206 | 0.181 | −0.785 | — |

Figure 15A:
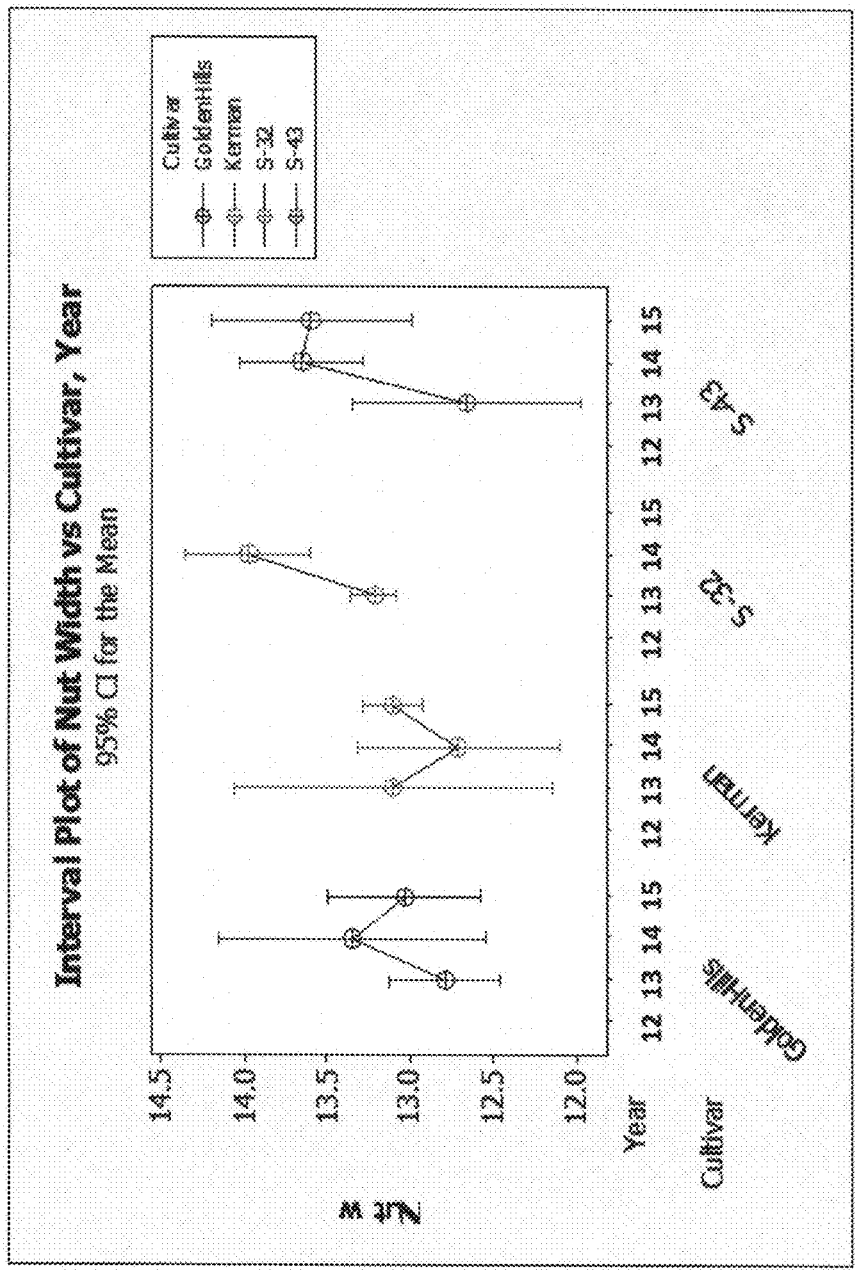
FIG. 15A illustrates nut width (mm) for 'Golden Hills', 'Kerman', 'Gumdrop' ('S-43'), and 'S-32' over several years (Years 13-15).
Figure 15B:
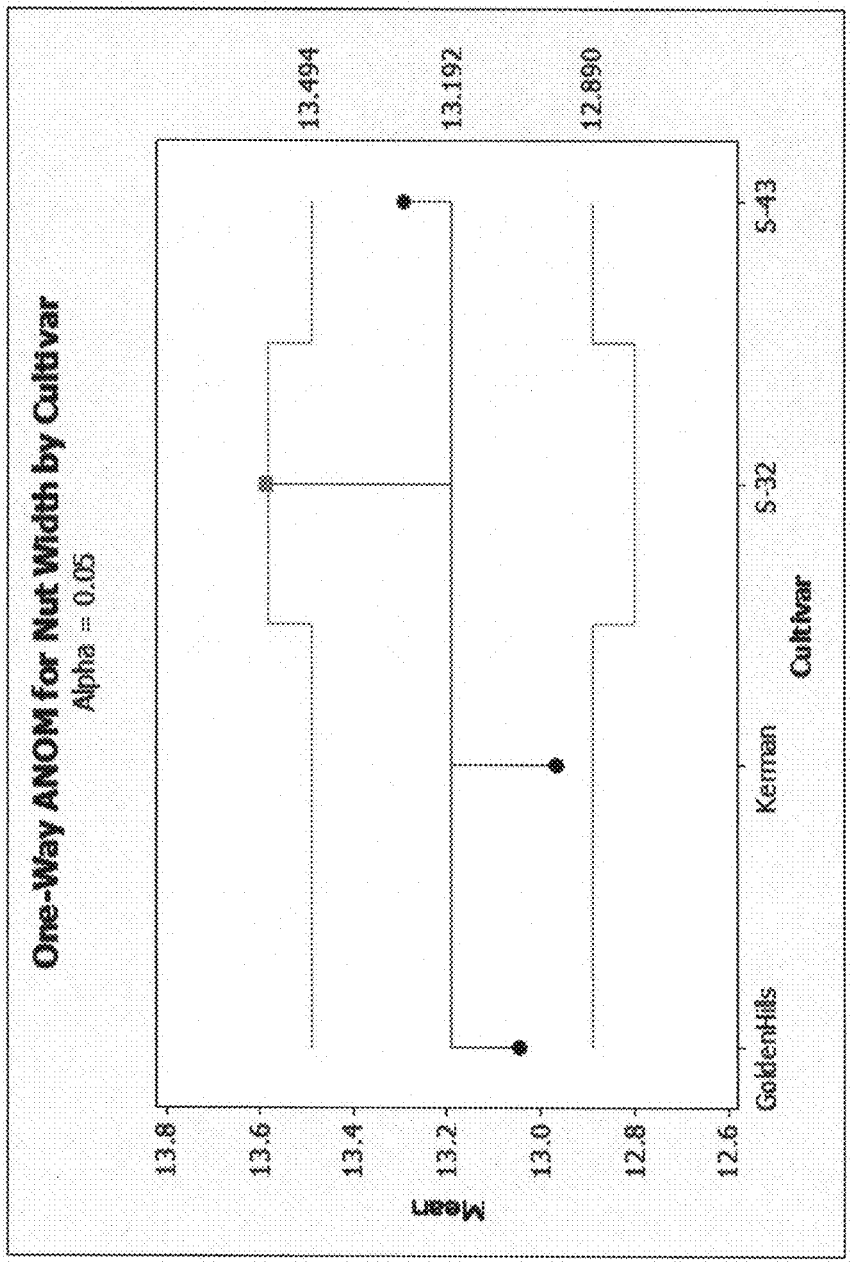
FIG. 15B illustrates an analysis of means for nut width (mm) for 'Golden Hills', 'Kerman', 'Gumdrop' ('S-43'), and 'S-32' over several years (Years 13-15). 'Gumdrop' trees were 6 years old in Year 13.

In terms of nut width, no significant differences in nut width were observed between 'Gumdrop' ('S-43'), 'Golden Hills', and 'Kerman' (13.3 mm, 13.1 mm, and 13.0 mm, respectively), with 'Gumdrop' having the greatest width (FIG. 15A and FIG. 15B). However, 'S-32' was significantly different than the other cultivars for both length and width, having a larger nut than the other cultivars. An analysis and statistics summary is provided in Table 12A and Table 12B.

TABLE 12A

Analysis of Variance for Nut Width

| Source | DF | Adj MS | F | P |
|---|---|---|---|---|
| Cultivar | 3 | 0.6373 | 5.31 | 0.006 |
| Year | 2 | 0.8152 | 6.80 | 0.004 |
| Block | 2 | 0.0057 | 0.05 | 0.954 |
| Error | 25 | 0.1199 | | |
| Total | 32 | | | |

S = 0.346327
R-Sq = 52.64%
R-Sq(adj) = 39.38%

TABLE 12B

Mean differences for nut width (lower diagonal) and P values (upper diagonal) for Bonferroni pairwise comparisons

| | Golden Hills | Kerman | S-32 | S-43 |
|---|---|---|---|---|
| Golden Hills | — | 1.0000 | 0.0204 | 0.8498 |
| Kerman | −0.081 | — | 0.0070 | 0.3290 |
| 5-32 | 0.610 | 0.691 | — | 0.3969 |
| S-43 (Gumdrop) | 0.248 | 0.329 | −0.362 | — |

What is claimed is:

1. A new and distinct variety of pistachio tree designated 'Gumdrop' as shown and described herein.

* * * * *